US010521559B1

United States Patent
Soumi et al.

(10) Patent No.: US 10,521,559 B1
(45) Date of Patent: Dec. 31, 2019

(54) ADVANCED HEALTHCARE INFORMATION ROUTING AND DELIVERY SYSTEMS AND METHODS OF USE AND DOING BUSINESS

(71) Applicant: Advanced Health Communications, L.L.C., Las Vegas, NV (US)

(72) Inventors: E. Ed. Soumi, Las Vegas, NV (US); Matthew Pham, Las Vegas, NV (US); Cesar Omar Gonzalez, Las Vegas, NV (US)

(*) Notice: Subject to any disclaimer, the term of this patent is extended or adjusted under 35 U.S.C. 154(b) by 280 days.

(21) Appl. No.: 14/304,675

(22) Filed: Jun. 13, 2014

Related U.S. Application Data

(60) Provisional application No. 61/892,590, filed on Oct. 18, 2013.

(51) Int. Cl.
*G16H 40/20* (2018.01)
*G06F 19/00* (2018.01)

(52) U.S. Cl.
CPC ......... *G06F 19/3418* (2013.01); *G16H 40/20* (2018.01)

(58) Field of Classification Search
CPC ...... G06Q 50/22; G06Q 50/24; G06F 19/322; G06F 19/327; G06F 19/30; G06F 19/34;
(Continued)

(56) References Cited

U.S. PATENT DOCUMENTS 5,283,856 A  2/1994  Gross et al.
6,961,559 B1 * 11/2005  Chow ............... H04M 3/42314
                                                         455/414.1
(Continued)

FOREIGN PATENT DOCUMENTS

WO  WO 2012/093307  *  7/2012 ............. H04L 12/58

OTHER PUBLICATIONS

Eze, et al.; Policy-based Data Integration for e-Health Monitoring Processes in a B2B Environment: Experiences from Canada; Journal of Theoretical and Applied Electronic Commerce Research; Apr. 2010.
(Continued)

*Primary Examiner* — Jason S Tiedeman
(74) *Attorney, Agent, or Firm* — Holland & Hart LLP

(57) ABSTRACT

An advanced healthcare information routing and delivery system and method of use and doing business. Some embodiments provide medical professional rule-based message routing and delivery of messages. In some embodiments, the system stores, retrieves, evaluates, and applies one or more medical professional on-call coverage routing rules, message delivery procedure rules, or rule application filters. In some embodiments, the system automatically routes messages to target devices based on the application of medical professional on-call coverage routing rules, delivery procedure rules, or both. In some embodiments, rule application is determined, in part, by prioritized rule application filters. In some embodiments, medical professionals, end users, and system administrators can configure rules, rule application filters, or both in real time via mobile device interfaces, workstation interfaces, or browser-based interfaces. In some embodiments, the systems can be used to provide novel business methods in the field of healthcare message routing and delivery.

8 Claims, 24 Drawing Sheets

(58) Field of Classification Search
CPC .... G06F 19/3418; G06F 19/363; G06F 19/36; G16H 40/00; G16H 40/20
USPC .......................................................... 705/2, 3
See application file for complete search history.

(56) References Cited

U.S. PATENT DOCUMENTS

| | | | |
|---|---|---|---|
| 7,034,691 B1* | 4/2006 | Rapaport | G06Q 10/10 340/573.1 |
| 7,630,371 B2 | 12/2009 | Hernandez et al. | |
| 7,702,523 B2 | 4/2010 | Sameh | |
| 7,742,762 B1 | 6/2010 | Biere et al. | |
| 7,809,584 B2* | 10/2010 | Morag | G06F 19/324 705/2 |
| 8,127,001 B1* | 2/2012 | Sylvain | G06Q 50/22 709/224 |
| 8,396,802 B2 | 3/2013 | Dala et al. | |
| 8,571,884 B2 | 10/2013 | Badgett et al. | |
| 8,639,531 B2* | 1/2014 | Hasan | G06Q 10/00 705/3 |
| 8,699,688 B2 | 4/2014 | Wellons et al. | |
| 10,210,952 B2* | 2/2019 | Reddy | H04M 3/42059 |
| 2002/0023172 A1 | 2/2002 | Gendron et al. | |
| 2003/0191663 A1* | 10/2003 | Sameh | G06Q 50/24 705/2 |
| 2003/0212575 A1* | 11/2003 | Saalsaa | G06Q 10/10 705/2 |
| 2004/0010423 A1* | 1/2004 | Sameh | G06F 19/328 705/2 |
| 2004/0125938 A1* | 7/2004 | Turcan | H04M 3/5183 379/265.02 |
| 2004/0181685 A1* | 9/2004 | Marwaha | H04L 41/0686 726/22 |
| 2004/0193447 A1* | 9/2004 | Joseph | G06Q 10/10 705/2 |
| 2004/0210457 A1* | 10/2004 | Sameh | G06Q 50/22 705/2 |
| 2005/0282566 A1* | 12/2005 | Bixler | G06F 19/3418 455/466 |
| 2006/0031101 A1* | 2/2006 | Ross | G06F 19/3418 705/3 |
| 2008/0004904 A1* | 1/2008 | Tran | A61B 5/0006 705/2 |
| 2009/0213852 A1* | 8/2009 | Krishnamurthi | H04L 51/14 370/389 |
| 2009/0222539 A1* | 9/2009 | Lewis | G06F 19/3481 709/221 |
| 2010/0069043 A1* | 3/2010 | Khawand | 455/412.1 |
| 2010/0211644 A1* | 8/2010 | Lavoie et al. | 709/206 |
| 2010/0269049 A1* | 10/2010 | Fearon | G06Q 10/109 715/744 |
| 2010/0286997 A1* | 11/2010 | Srinivasan | G06Q 50/22 705/2 |
| 2011/0001605 A1 | 1/2011 | Kiani et al. | |
| 2011/0004491 A1* | 1/2011 | Sameh | G06F 19/3418 705/3 |
| 2011/0119088 A1* | 5/2011 | Gunn | G06Q 50/24 705/3 |
| 2012/0092157 A1* | 4/2012 | Tran | G06F 19/3418 340/539.12 |
| 2012/0095779 A1* | 4/2012 | Wengrovitz | G16H 40/20 705/2 |
| 2012/0115448 A1* | 5/2012 | Rosenhaft | G06Q 10/087 455/414.1 |
| 2013/0167173 A1* | 6/2013 | Davis et al. | 725/37 |
| 2013/0173719 A1 | 7/2013 | Ahmed et al. | |
| 2013/0275539 A1* | 10/2013 | Gross | H04L 12/1895 709/206 |
| 2014/0039912 A1 | 2/2014 | Turinas et al. | |
| 2014/0126569 A1 | 5/2014 | Deich et al. | |
| 2015/0066525 A1* | 3/2015 | Webb, III | G06F 19/322 705/2 |

OTHER PUBLICATIONS

Alain Mouttham, et al; Event-Driven Data Integration for Personal Health Monitering; Journal of Emerging Technologies in Web Intelligence; Nov. 2009.

Fran Turisco; Save money and increase efficiency through Intranet-based physician paging; Healthcare Financial Management; Aug. 1999.

* cited by examiner

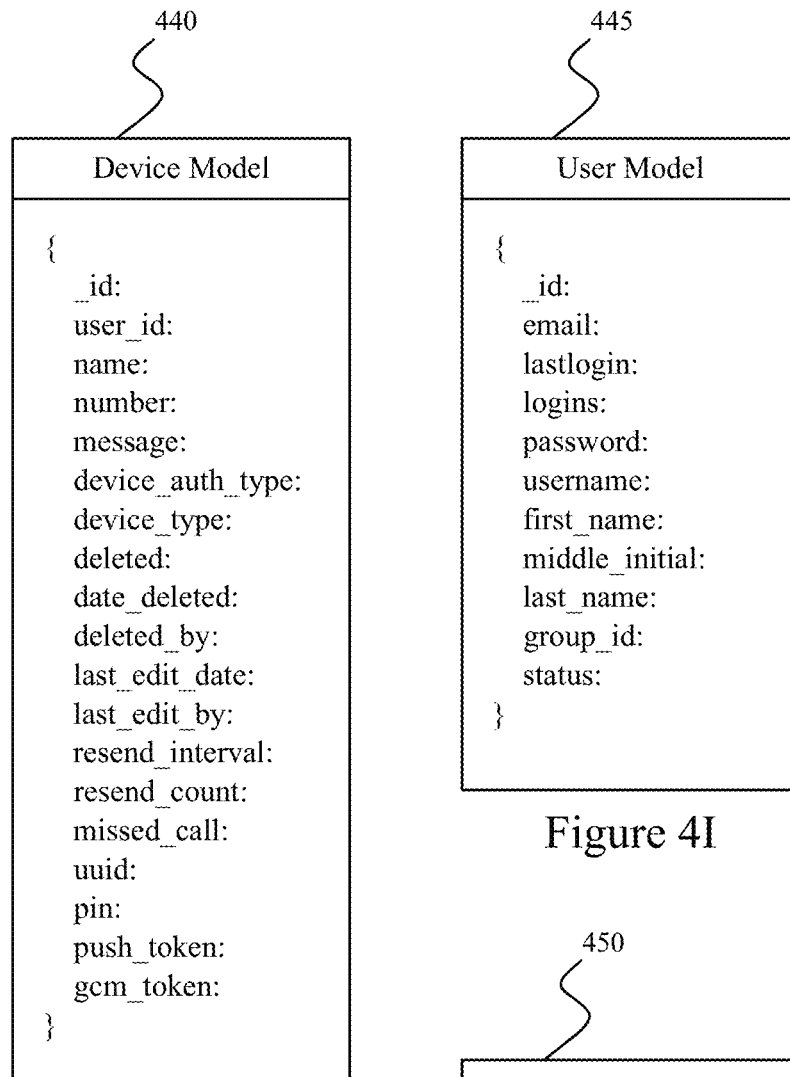
Figure 4H
Figure 4I
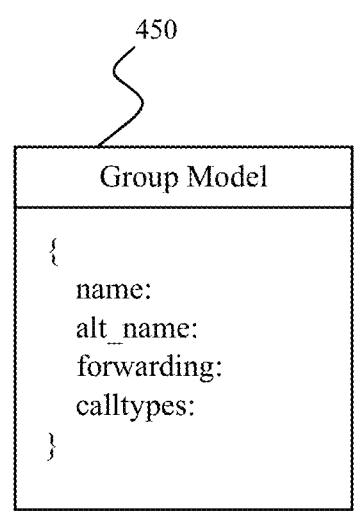
Figure 4J

Figure 10

✓ All Call Types
  Coroner's Office
  Nurse
  Physician
  Unit Coordinator
  Group Admin
  Group Operator
  Group Billing Admin
  Provider (Physician)
  InPatient or Family Member
  OutPatient or Family Member
  InPatient Pharmacy
  Outpatient Pharmacy
  Quest Diagnostics & Other Labs
  OutPatient Radiology
  Home Health Agency
  Patient Scheduling
  Patient Cancellations
  Referrals
  Family Medical Leave ACT (FMLA)
  Medical Prior Authorizations
  Insurance Prior Authorizations
  Mortuary
  Personal Calls
  Chief of Medicine
  Prisoner
  Executive Health Resources
  Outpatient Medical Records
  Inpatient Medical Records

Figure 14

Message Log    [Search] [View 100]

| Message | Info & Options |
|---|---|
| To:    Cesar Gonzalez  Message: test<br>From:  Guest: test  Patient:  test test<br>Sent By:  Cesar Gonzalez<br>Facility:<br>Desert Springs Hospital Medical Center CDU<br>Callback:  (702) 894-5707<br>Agent:  Cesar Gonzalez<br>Calltype:  Nurse | [🔍] [⊘] [☑]<br>Sent:<br>05/20/14 03:23 PM<br>Confirmed:<br>  Unconfirmed<br>Device:  conf<br>Response:<br>  No response<br>Confirmed By:<br>  Unconfirmed |
| To:  IPC Test Dr.  Message: test<br>From:  Guest: Joe  Patient:  john doe<br>Sent By:  nurse betty<br>Facility:<br>  Centennial Hills Hospital 6S<br>Callback:  (702) 629-1214<br>Calltype:  Unit Coordinator | [🔍]<br>Sent:<br>05/07/14 10:37 AM<br>Confirmed:<br>05/21/14 02:01 PM<br>Device:  SMS<br>Response:<br>  No response<br>Confirmed By:<br>  IPC Admin |
| To:  IPC Test Dr.  Message: Abnormal Lab results. k lvl 7.9<br>From:  Guest: Jane  Patient:  Johnathan Smith<br>Sent By:  nurse betty<br>Facility:<br>  Centennial Hills Hospital 6S<br>Callback:  (702) 629-1214<br>Calltype:  Unit Coordinator | [🔍] [⊘] [☑]<br>Sent:<br>05/07/14 10:11 AM<br>Confirmed:<br>  Unconfirmed<br>Device:  SMS<br>Response:<br>  No response<br>Confirmed By:<br>  Unconfirmed |
| To:<br>Test Discharged / Transferred Patients<br>From:  Guest: Tom<br>Sent By:  nurse betty | Message: PT transferred to Complex care SNF.<br>Patient:  john doe | [🔍]<br>Sent:<br>05/07/14 10:03 AM |

Figure 19

ADVANCED HEALTHCARE INFORMATION ROUTING AND DELIVERY SYSTEMS AND METHODS OF USE AND DOING BUSINESS

CROSS-REFERENCE TO RELATED APPLICATIONS

This application claims priority through the applicants' provisional application titled MESSAGING SYSTEMS AND METHODS, filed Oct. 18, 2013, Application No. 61/892,590, which is hereby incorporated by reference in its entirety.

COPYRIGHT NOTICE

This patent document contains material subject to copyright protection. The copyright owner has no objection to the photocopy reproduction of the patent document or the patent disclosure in exactly the form it appears in the Patent and Trademark Office patent file or records, but otherwise reserves all copyright rights.

FIELD OF TECHNOLOGY

The present application relates to message delivery systems and methods for health care professionals and, in some embodiments, to rule-based message routing in such systems and methods.

APPLICANTS' VIEW OF SOME ASPECTS OF PRIOR SYSTEMS

Historically, communications between nurses and doctors have been inefficient, slow, and error-prone. The conventional method of contacting a doctor regarding patient treatment at a hospital generally required a nurse (or another person) to call a physician's answering service. A call center representative would record a message for the doctor based on the call from the nurse, then attempt to contact the doctor, often by placing multiple phone calls to different numbers.

This conventional method can be time consuming, particularly for the nurse attempting to contact the physician. The nurse makes a phone call and leaves a message, then waits for the call center to ascertain the correct number to reach the physician. Often, the nurse or other caller is required to wait on hold until a call center agent is available to take the nurse's call. This equates to a long wait time before the doctor receives the message. Further, these inefficiencies in communication can directly impact the time between a nurse attempting to contact a physician and the time when the patient receives care, and can potentially have serious consequences for patients in need of urgent care.

It addition, traditional systems, while providing some message processing for on-call professionals for example, have lacked robust capabilities to facilitate timely routing of messages to the correct recipients. For example, modern advancements in communications methods include, but are not limited to, text messaging, app messaging, conference calling, mobile calling, voice-to-text email transcription, and the like. At any given time, one of these delivery methods may be preferred by a physician based on, for example, the activity in which they are engaged at the time. Systems that have relied on unintelligent general transmission of messages to fixed message destinations such as phone numbers and pagers have not provided a way to deliver messages to the physician using the method most likely to provide the physician with the ability to consume the message and respond in a timely manner. This often has resulted in nurse and physician frustration as receipt of messages was delayed in both directions.

Yet another shortcoming of traditional call-center messaging systems has been the limited ability to process high call volume absent a large number of available call center agents. For example, if 100 nurses call a call center where only 6 call center agents are answering phones, then only 6 calls are processed at any given time, and the remaining calls are placed on hold (remain in the queue) until the agents are free to answer the queued calls. The amount of time the nurse or callers are on hold in the queue increases as call volume increases, impacting time to treatment, as well as the overhead costs associated with obtaining treatment.

Further exacerbating this problem is the common situation in which the doctor is unavailable or there is a delay in response that is not visible to the calling nurse. The delay in delivering the message to the correct physician, the correct physician then receiving and responding to the message, or both, can further delay patient care. This is due, in part, to the nurse possibly repeating the entire process of calling the call center, waiting for an agent to answer, waiting for a response from a physician, and the like.

The manual aspects of conventional call center agent involvement can also have a negative impact on the efficiency and accuracy of message routing. For example, message relay by a call center agent typically involves decisions about routing, message interpretation, or both. A call from a nurse may require the call center agent to take notes that lack accuracy or completeness such that the message being transmitted is insufficient for the physician to respond appropriately. This can require a second round of message interaction that might have otherwise been avoided, delaying care and frustrating the healthcare professionals involved. Further, static routing systems and systems that rely on call center agents to make routing decisions can result in messages being sent or calls being made to the improper physician, creating further inefficiencies.

These traditional solutions have generally lacked granularity with respect to how different types of calls are processed. For example, calls from a particular location or person, calls about a particular patient, or calls indicating a particular type of patient status each might need to be processed and delivered differently. In addition, the way this processing and delivery should occur may change at any given time based on varying circumstances, including those specific to the physician such as their temporary unavailability for example. Systems lacking the ability to control the processing and delivery at a granular level in real time and from any location can result in delays, and in some circumstances failure, in delivering messages to the appropriate physician in the manner best suited for the physician's consumption of the message.

Doctors and other medical professionals have long been carrying mobile phones with them as they work, are on call, and otherwise. These phones have long had substantial messaging and other capabilities, such as the ability to run a wide variety of applications. The adoption of tablets in many practices has further placed more powerful communication capabilities in the hands of nurses and physicians. Nevertheless, the existing communications systems for doctors and nurses, for example, remain subject to issues such as noted above.

BRIEF SUMMARY OF SOME ASPECTS OF THE PRESENT SYSTEM AND METHODS

The applicants believe that they have discovered at least one or more of the problems and issues with prior art systems noted above as well as one or more advantages provided by differing embodiments of the system or system features disclosed in this specification. In addition, the applicants have identified communication-based needs for greater efficiency in physician responsiveness, improvement of patient care in hospitals, reduction in hospital and physician overhead costs, reduction in human errors, and increased overall collaboration levels between health care professionals.

Briefly and in general terms, the present disclosure provides for a rule-based message routing and delivery system for the automated routing and delivery of messages. In some embodiments, this system is based, at least in part, on on-call coverage routing rules, message delivery procedure rules, and rule application filters.

In some embodiments, the rule-based message routing and delivery system receives and automatically routes messages based on the application of on-call coverage routing rules, delivery procedure rules, or both. End users and system administrators can configure these rules in real time via mobile device interfaces, workstation interfaces, browser-based interfaces, and the like.

In certain instances, the application of these rules is determined, in part, by configurable application filters. The rules and filters can be stored in database servers and made accessible to multiple devices in multiple locations. The ability to retrieve and configure these rules in real-time from any location via a mobile device can, in some applications, allow healthcare professionals to tailor routing and delivery of messages to accommodate their particular objectives. This can afford physicians, for example, the opportunity to create and modify rules so that messages are correctly routed upon initial routing, thus reducing aggravation with misdirected messages and improving turnaround time for care requests. In addition, this also provides the physician with the ability to configure their own delivery preferences, such as the type of messaging employed and the destination device targeted based on certain conditions being met relating to, for example, call type, message content, and the like. Here too, this delivery procedure customization can reduce delays and enhance the physician experience, thus encouraging improved collaboration among healthcare professionals, as well as between patients, nurses, and physicians.

In some embodiments, delivery methods can include one or more of the following:
  a) delivery of SMS messages to mobile devices;
  b) delivery of secure SMS messages via secure links to mobile devices;
  c) delivery of transcribed voice message as a secure SMS message to mobile devices;
  d) delivery of app messages to mobile devices;
  e) delivery of messages to system message inboxes;
  f) relay of messages by a call center agent; and
  g) initiation of a conference call with a message originator.

Making available various different types of messaging options, and taking advantage of mobile technology and hosted messaging services, can provide increased opportunities for automated routings that facilitate direct communication between nurses and physicians, thus reducing the overhead costs associated with facilitating such communications via traditional systems. Offering such a varied selection of messaging options can encourage the use of mobile devices in the context of healthcare communication, thus improving the degree and quality of collaboration among healthcare professionals.

In certain instances, for example, through a mobile app, a physician or practice manager may configure the rule-based message routing and delivery system to send the physician a text message, such as, for example, a secure SMS message, when a particular nurse sends a message to the physician. The system can send the message to that physician's mobile devices, such as her or his cell phone or tablet. However, if the physician instead directs the system to inform him of messages by phone call, then the message that originates from the nurse can be directed to a call center and the call center can call the physician with the message or, if requested by the doctor, call the nurse and conference the nurse onto the call. In addition, in some cases, the doctor can direct the system to transcribe calls originating from, for example, a nurse and send the transcribed message as a secure SMS message.

In some embodiments, the rule-based message routing and delivery system stores configurable rule application filters that can determine, in part, the application of on-call coverage routing rules, delivery procedure rules, or both. In certain instances, default message fields, custom message fields, or both, can be used for the construction of filter conditions. Rule application processing can include, in part, the retrieval of associated rules from a central repository such as, for example, a central database, the retrieval and evaluation of application filters associated with the rules, the pooling of application filters that match the message input value of the filter conditions, the prioritization of the pooled application filters, the identification of high priority application filters, and the application of a high or highest priority application filter. The rule-based message routing and delivery system can then route and deliver the message based on the appropriate on-call coverage and delivery procedures, thus improving the likelihood that the physician will receive the message and respond in a timely manner. This can reduce the chance that physicians who are not on call receive incorrect notifications, thus reducing physician frustrations and communication inefficiencies. Further, to the extent the physician participates in rule and filter configuration, the physician's delivery procedure preferences can direct, at least in part, how the physician will be contacted based on the physicians needs and preferences at the time.

There are many different types of preferences and procedures that varying embodiments of the system can allow users or administrators to configure through the app, a workstation interface, a browser interface, and the like. In some systems, users may select preferences and procedures through the mobile app such that the following types of routings and deliveries occur through the rule-based message routing and delivery system. For example, users may establish procedures as follows:
  a) a physician may receive a message via text (such as via secure SMS) when the message originates from a nurse, but if a message comes from a pharmacy, the rule-based message routing and delivery system instead directs the message to a person at a call center for connecting the physician to the pharmacist via conference call;
  b) a physician may receive relayed phone calls on her or his home phone during selected evening hours but otherwise receive text messages on her or his mobile device;
  c) a physician may receive a transcribed message via text message if a hospital (or other health care facility) nurse calls, but all other calls may be diverted to the physician's group administrator;

d) a call may be routed to another physician, such as a physician on call, for example, if the patient is an existing patient and a custom message field value indicates the condition relates to seizures;
e) a physician may receive text messages when messages originate from one hospital, but when messages originate from a different hospital, the messages are routed to the physician's partner, unless the message is identified as urgent, in which case it is delivered to the physician; and
f) a physician may send a message (or a consult) to another physician and, if that physician is unavailable, the consult or message is forwarded to an on-call physician.

In some embodiments, the rule-based message routing and delivery system can process many more calls than systems and methods that rely on traditional call centers. In some applications, thousands of calls can be processed within seconds, such as by routing calls and messages from nurses, for example, directly to the physician, as another example. Such systems can improve physician responsiveness, collaboration between health care providers, and patient care, while reducing health care operating costs and human error.

In certain applications, the rule-based message routing and delivery system and application operator can provide a unique business model that integrates call center systems with those of the health care facilities and health care professionals, via the mobile app, to provide call handling, message delivery, and HIPAA compliant communication tools for subscribers to these systems and services. In some instances, this integration involves limited setup, instead leveraging existing technology and devices, allowing healthcare professionals to augment existing procedures with little to no additional capital expense or inter-system dependency. Nurses, for example, can conveniently login to any computer and instantly send secure direct messages to participating physicians. This can allow for rapid deployment and easy user adoption with minimal disruption, all without increasing risk that might otherwise result from hard-coded, system-to-system integrations.

At least some embodiments can thus provides robust automated message routing and delivery functionality along with mobile communications and control capability, including capabilities provided by a mobile app. Using the mobile app, in some applications, the health care professionals can communicate and collaborate with each other regarding patient care much more effectively and rapidly than with prior systems. In some instances, based at least in part on the applied delivery procedures, health professionals can communicate with one another and with patients directly, entirely bypassing call center operations. In some instances, the call center can facilitate communications, processing messages much more efficiently, quickly, and accurately. When the system provides the mobile app user, or persons working with the mobile app system, the ability to control how others communicate with the user through the system, communications can be much more reliably accomplished and tracked, and the mobile app user, such as a physician, can manage communications regarding patients much better than with prior systems.

The scope of the inventive features disclosed in this specification is not limited to the features described in this brief summary or to addressing issues noted in the "Applicants' View Of Some Aspects Of Prior Systems" above. There are many other novel aspects, problem solutions, and advantages of the systems disclosed in this specification. They will become apparent to those skilled in the art as this specification proceeds.

BRIEF DESCRIPTION OF THE DRAWINGS

The applicant's preferred and other embodiments are disclosed in association with the accompanying Figures. In the Figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 4A through FIG. 4J are diagrams of various models of the persistence layer of FIG. 3 according to an exemplary embodiment.

FIG. 10 is a screen capture of a portion of new filter creation page for interfacing with the filter service of FIG. 3.

FIG. 14 is a screen capture of the selection dialog displaying the call types that correspond to the call type icons of FIG. 13.

FIG. 19 is a screen capture of a call center agent message log page displaying the call history retrieved from the message service of FIG. 3.

DETAILED DESCRIPTION OF THE DRAWINGS

Figure 1:
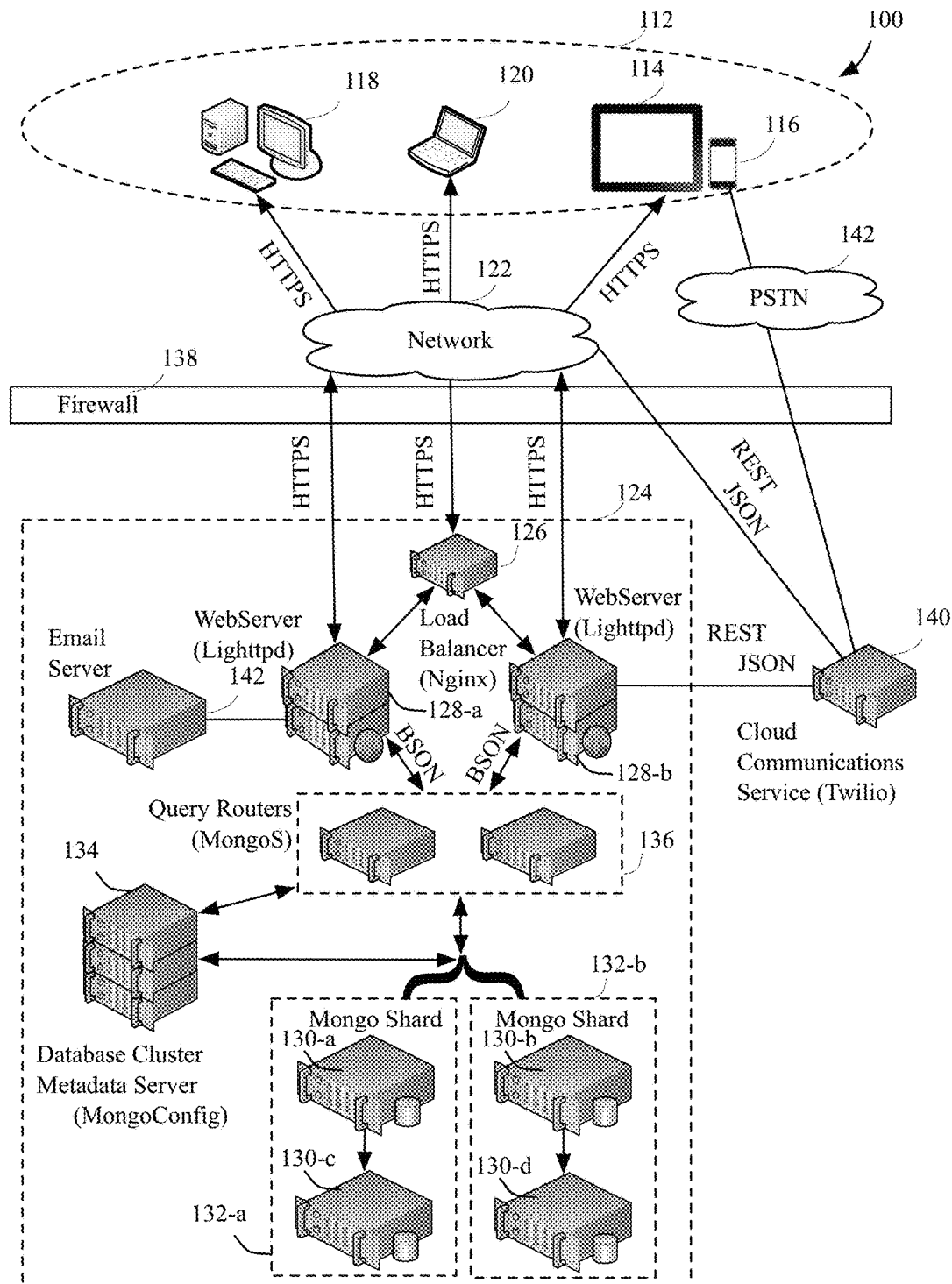
FIG. 1 is a computer network or similar digital processing environment in which a rule-based message routing and delivery system can be implemented according to an exemplary embodiment.

Certain embodiments of the rule-based message routing and delivery system and methods are described with reference to methods, apparatus (systems), and computer program products that can be implemented by computer program instructions. These computer program instructions can be provided to a processor of a general purpose computer, special purpose computer, mobile computing device, or other programmable data processing apparatus to produce a machine, such that the instructions, which execute via the processor of the computer or other programmable data processing apparatus, create means for implementing the acts specified herein to transform data from a first state to a second state.

These computer program instructions can be stored in a computer-readable memory that can direct a computer or other programmable data processing apparatus to operate in a particular manner, such that the instructions stored in the computer-readable memory produce an article of manufacture including instruction means which implement the acts specified herein. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the acts specified herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any conventional processor, controller, microcontroller, or state machine. A processor can also be implemented as a combination of computing devices such as, for example, a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a computer terminal. In the alternative, the processor and the storage medium can reside as discrete components in a computer terminal.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently such as, for example, through multi-threaded processing, interrupt processing, or multiple processors or processor cores, rather than sequentially. Moreover, in certain embodiments, acts or events can be performed on alternate tiers within the architecture.

Referring now to FIG. 1, a computer network or similar digital processing environment 100 in which the systems and methods disclosed can be implemented. The present systems and methods can also run on different architectures that may include a LAN, WAN, stand-alone PC, stand-alone mobile device, a stand-alone, clustered, or networked mini or mainframe computers, etc. The rule-based message routing and delivery system and method of use can be distributed on multiple computers and devices 112, 124.

FIG. 1 is only an example, however, as many other computing arrangements can support the systems and methods disclosed in this specification. Further, the system shown in FIG. 1 can utilize a wide variety of differing sub-systems in order to support the disclosed systems and methods.

For example, in one embodiment, the software implementing the rule-based message routing and delivery system runs in the Linux® environment. In another embodiment, the software is implemented to run in other environments, such as Windows®, UNIX®, and may run on any hardware having enough power to support timely operation of software such as that identified in FIG. 1. In certain instances, computers are deployed as virtual instances rather than physical computers.

An http load balancing router 126, such as for example, Nginx® can distribute traffic inside a firewall 138 to and from web server computers 128, which can improve performance, scalability and reliability of the rule-based message routing and delivery system. Load balancing strategies may include, for example, round-robin request distribution, least number of active connections distribution, or ip-hash function distribution.

In some deployments, web servers 128 are instances of Lighttpd with PHP packages, deployed with fastcgi module and php configuration enabled. Those skilled in the art will appreciate that other web server and application server technologies can be used as an alternative to Lighttpd. The load balancer 126 and webservers 128 communicate with one another, and with client devices and instances, over HTTPS. Other protocols may be used depending on the technology stack deployed. The webservers can communicate with the database instances via the transmission of BSON (Binary JavaScript Object Notation) objects using a PHP driver object designed to specifically facilitate database interactions, such as database reads and writes.

Database servers, in some embodiments, can deploy schemaless non-relational databases, such as MongoDB, storing information as documents rather than as records in tables. Alternatively, relational databases with traditional schema restrictions can be implemented, such as Microsoft SQLServer®, MySQL®, and SQLLite. In certain implementations, the database deployment can be implemented in a sharded cluster 132. The shards 132 store the data, providing high availability and data consistency, with each shard 132 including a replica data set 132-c, 132-d. The replica sets 132-c, 132-d are a group of database instances that host the same data set. One database instance for each of the primaries 130-a, 130-b receives all write operations. All other instances, secondaries 130-c, 130-d, apply operations from the primary so that they have the same data set. The primaries 130-a, 130-b accept all write operations from clients.

To support replication, the primaries 130-a, 130-b log all changes to their data sets in its oplog. The secondaries 130-c, 130-d replicate the primary's oplog and apply the operations to their data sets. Secondaries' data sets reflect the primary's data set. If the primary, e.g., 130-a is unavailable, the replica set will elect a secondary, e.g., 130-c, to be primary. By default, clients 112 read from the primaries 130-a, 130-b; however, clients can specify a read preferences to send read operations to secondaries 130-c, 130-d in some instances.

In some implementations, config servers 134, such as MongoConfig are special database instances that store the metadata for a sharded cluster. This data contains a mapping of the cluster's data set to the shards 132. The query router uses this metadata to target operations to specific shards. Config servers 134 can use a two-phase commit to achieve immediate consistency and reliability. Config servers 134 do not run as replica sets. All config servers 134 are available to deploy a sharded cluster 132 or to make any changes to cluster metadata. In some deployments, a sharded cluster 132 has three config servers 134.

One or more query routers 136, such as MongoS, can be deployed in certain instances. Query routers interface with client applications and direct operations to the appropriate shard or shards 132. The query router 136 processes and targets operations to shards 132 and then returns results to the clients 112 via the web servers 128. A sharded cluster 132 can contain more than one query router 136 to divide the client request load. A client 112 sends requests to one query router via the web servers 128. Sharded clusters 132 can have many query routers 136.

In certain implementations, the web servers 128 interface with a cloud communication service server 140, such as Twilio®, over a REST API using JSON objects. The cloud communication service server 140 can, for example, support querying meta-data about an account, phone numbers, calls, text messages, and recordings. It can also, in some instances, initiate outbound calls and send text messages over a public switched telephone network 142.

In some instances, an email server 142 may be communicatively coupled with the web servers 128 providing email send and receive support for messaging operations.

In some instances, properties in each model represent a column in the database, even though MongoDB is a schemaless, non-relational database. When a call is made to save a model, each changed property is updated in the database. When a model is loaded, the columns specified in the model are loaded from the database and a new PHP object is created with the columns as properties with the corresponding values.

Client computing devices of various types 112 can connect to a remote server infrastructure 124 via a network 122 over a communication protocol. All computing devices can pass information as unstructured data, structured files, structured data streams such as, for example, XML, structured data objects, and/or structured messages. Client computing devices 118, 120, 114, 116 may communicate over various protocols such as, for example, UDP, TCP/IP, and/or HTTPS.

Client computing devices 118, 120, 114, 116 and server computers 124 provide processing, storage, and input/output devices executing application programs. Client computers 112 can also be linked through communications network 122 to other computing devices, including other client devices/processes 112 and server computers 124.

In some embodiments, server computers 132 run software to implement centralized persistent data storage and retrieval. The network 122 can be a local area network and/or a wide area network that is part of a remote access network, a global network (e.g., the Internet), a worldwide collection of computers, gateways that currently use respective protocols (TCP/IP, UDP, etc.) to communicate with one another, and the like. Multiple client computer devices 112 may each execute and operate instances of the applications accessing the rule-based message routing and delivery system servers.

Figure 2:
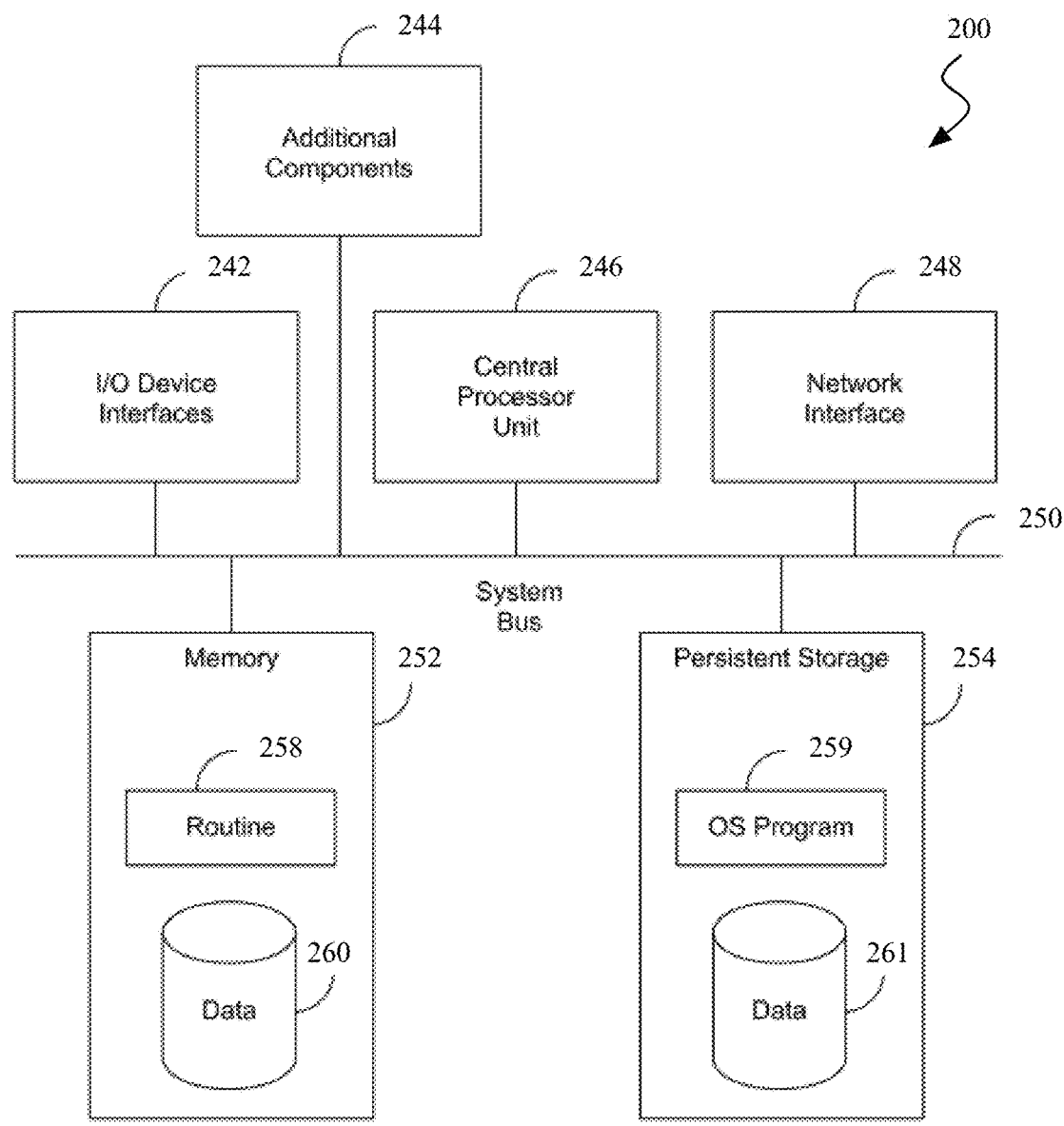
FIG. 2 is a block diagram of the internal structure of a computer used in the computer network of FIG. 1.

Referring now to FIG. 2, each component of the system 200 is connected to a system bus 250, providing a set of hardware lines used for data transfer among the components of a computer or processing system. Also connected to the bus 250 are additional components 244 of the rule-based message routing and delivery system, such as additional memory storage, digital processors, network adapters, and I/O devices. The bus 250 is essentially a shared conduit connecting different elements of a computer system (e.g., processor, disk storage, memory, input/output ports, network ports, etc.) and enabling transfer of information between the elements. An I/O device interface 242 is attached to system bus 250 in order to connect various input and output devices (e.g., keyboard, mouse, touch-screens, displays, printers, speakers, etc.) to rule-based message routing and delivery system. A network interface 248 allows the computer to connect to various other devices attached to a network (e.g., network 122 of FIG. 1). A memory 252 provides volatile storage for computer software instructions 258 and data 260 used to implement methods employed by the system disclosed herein. Disk storage 254 provides non-volatile storage for computer software instructions 259 and data 261 used to implement an embodiment of the present disclosure. A central processor unit 246 is also attached to system bus 250 and provides for the execution of computer instructions.

In one embodiment, the processor routines 258 and data 260 are a computer program product, including a computer readable medium (e.g., a removable storage medium such as one or more DVDROM's, CD-ROM's, diskettes, tapes, etc.) that provides at least a portion of the software instructions for the rule-based message routing and delivery system. A computer program product that combines routines 258 and data 260 may be installed by any suitable software installation procedure, as is well known in the art. In another embodiment, at least a portion of the software instructions may also be downloaded over a cable, communication, and/or wireless connection.

Figure 3:
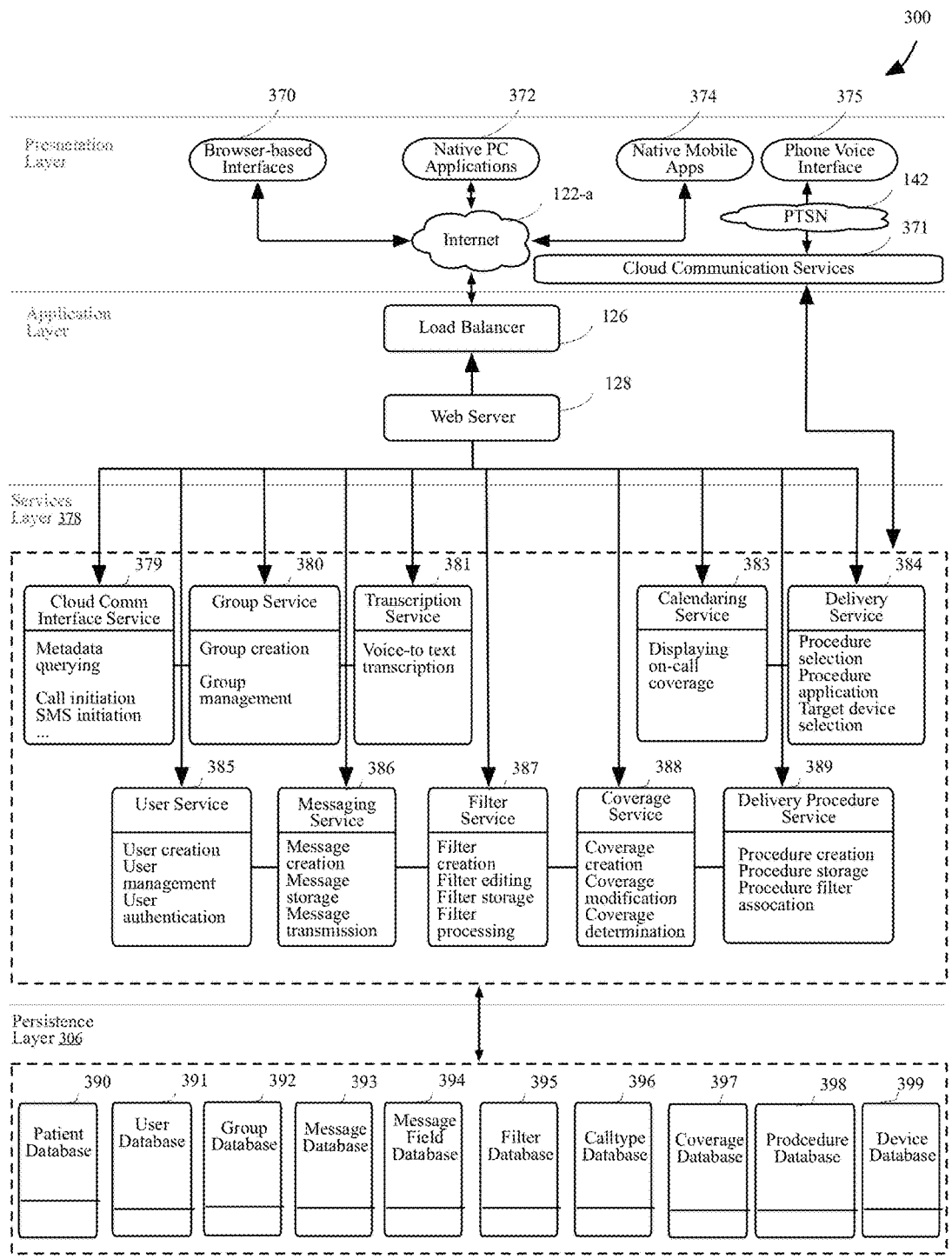
FIG. 3 is a service oriented architecture diagram of the rule-based message routing and delivery system in the embodiment of FIG. 1.

Referring now to FIG. 3, client devices can provide user interfaces to one or more of the functions of the rule-based message routing and delivery system services 378. Such interfaces can be browser-based, application-based, or both. In some embodiments, these applications can include application containers such as html clients 370, native computer applications 372, and/or native mobile apps 374. In addition, voice interfaces such as those provided by phone technologies 375 can be facilitated through cloud communication services 371.

The rule-based message routing and delivery system architecture 300 can include a services layer 378 that exposes a variety of discreet services accessible to authorized device interfaces 370, 372, 374, 375 and/or services. It is through these services 378 that information can be added to, and retrieved from, the databases found in the persistence layer 306. The services layer 378, together with the persistence layer 306, can, in part, consist of a collection of distributed classes and data stores providing the mobile information management system functionality.

In some embodiments, the cloud communication interface service 379 provides classes and/or associated methods and data structures for call metadata querying, message metadata querying, call recording metadata querying, call initiation, and text message initiation functions. These classes and/or methods are supported by data and document associations stored in a persistence layer 306, which can include a message database 393 and a device database 399.

The group service 380 can provide classes and/or associated methods and data structures for the group creation and group management functions. These classes and/or methods are supported by data and document associations stored in the persistence layer 306, which can include a user database 391 and a group database 392.

In certain implementations, the transcription service 381 provides classes and/or associated methods and data structures for voice-to-text transcription functions. These classes and/or methods are supported by data and document associations stored in the persistence layer 306, which can include a message database 393 and procedure database 398. In some implementations the cloud communication interface service 379 supports the transcribing functionality of this service.

In some instances, the calendaring service 383 provides classes and/or associated methods and data structures for displaying on call coverage. These classes and/or methods are supported by data and document associations stored in the persistence layer 306, which can include a coverage database 397.

A delivery service 384 provides classes and/or associated methods and data structures for delivery procedure processing and selection, delivery procedure application, and target device selection. These classes and/or methods are supported by data and document associations stored in the persistence layer 306, which can include a procedure database 398.

The user service 385 provides classes and/or associated methods and data structures for user creation, user management, and user authentication functions. These classes and/or methods are supported by data and document associations stored in the persistence layer 306, which can include a user database 391.

The messaging service 386 provides classes and/or associated methods and data structures for message creation, message storage, and message transmission functions. These classes and/or methods are supported by data and document associations stored in the persistence layer 306, which can include a message database 393, a message field database 394, and a patient database 390.

The filter service 387 provides classes and/or associated methods and data structures for filter creation, filter editing, filter storage, and filter processing functions. These classes and/or methods are supported by data and document associations stored in the persistence layer 306, which can include a filter database 395 and message fields database 394.

The coverage service 388 provides classes and/or associated methods and data structures for coverage creation, coverage modification, and coverage determination functions. These classes and/or methods are supported by data and document associations stored in the persistence layer 306, which can include a coverage database 397 and a filter database 395.

The delivery procedure service 389 provides classes and/or associated methods and data structures for procedure creation, procedure storage, and procedure filter association functions. These classes and/or methods are supported by data and document associations stored in the persistence layer 306, which can include a procedure database 398, a calltype database 396, a filter database 395, a user database 391, and a device database 399.

Referring now to FIG. 4A through FIG. 4J, an example set of database models as part of a schemaless database supporting the persistence layer 306 and the services layer 378 of the rule-based message routing and delivery system 100 is shown according to an exemplary embodiment (e.g., see FIG. 1 and FIG. 3). Properties in each model represent a column in the database, although the database may be a schemaless non-relational database such as MongoDB. When calling save on a model, each property is updated in the database. When a model is loaded, the columns specified in the model are loaded from the database and a new PHP object is created with the columns as properties with the corresponding values.

Figures 4A, 4B:
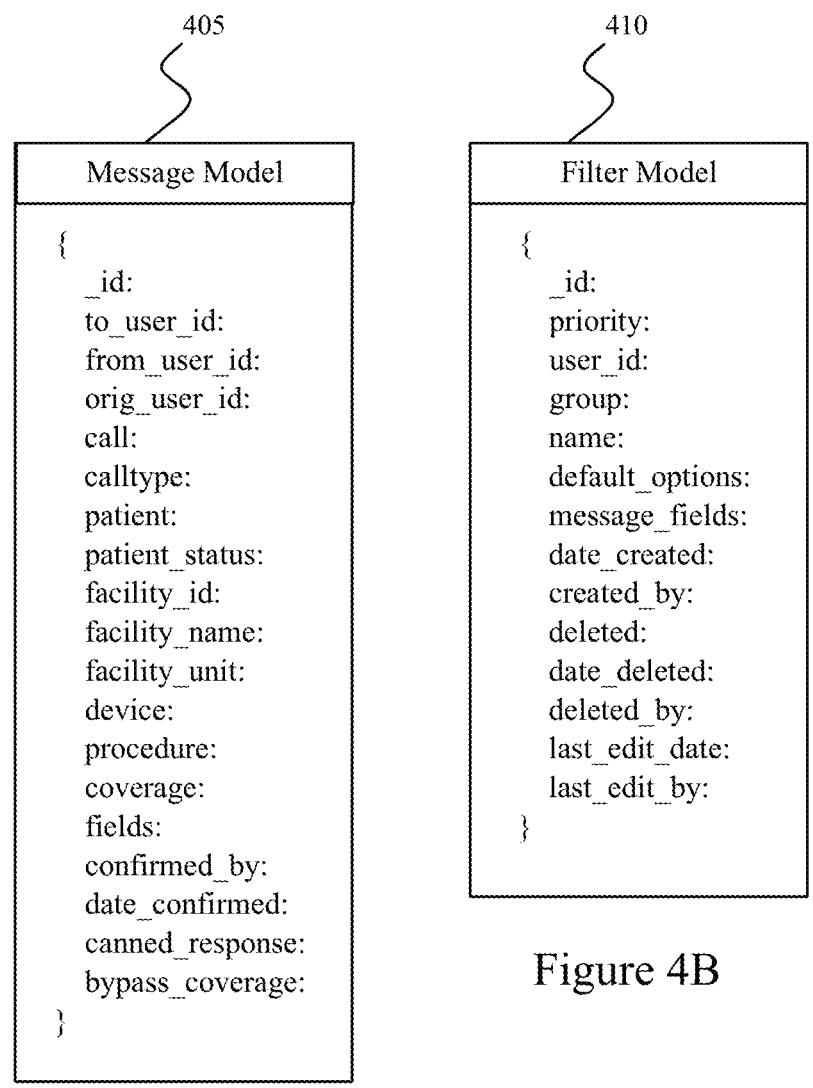

An example of a message model 405 as shown in FIG. 4A represents the communication delivered to the target device. Properties (i.e. columns) within the message model are listed and described below:

a) _id: this is the message model primary key and can be used to relate other documents to the message model;
b) to_user_id: this is the user model primary key for the user receiving the message, thus associating the message document to the user document;
c) from user_id: this can be the user model primary key for the user sending the message or the user model primary key of the individual selected by a call center agent, thus associating the message document to the user document;
d) orig_user_id: this is the user model primary key for the user selected as the message recipient by the message sender, thus associating the message document to the user document;
e) call: this is the call model primary key for the incoming call which initiated the message, thus associating the message document to the call document;
f) calltype: this is the calltype model primary key for the incoming call which initiated the message, thus associating the message document to the calltype document;
g) patient: this is the patient model primary key for the patient selected/entered by the sender, thus associating the message document to the patient document;

h) patient status: this is a textual representation of the patient status (e.g. new|established|none) as provided by the sender;
i) facility_id: this is the model facility primary key for the facility selected by the sender, thus associating the message document to the facilities document;
j) facility_name: this is the textual representation of the facility based on facility_id (e.g., Summerlin Hospital Medical Center);
k) facility_unit: this is the textual representation of the unit within the facility based on the facility_id (e.g., Pediatrics);
l) device: this is the device model primary key for the device which the message was delivered to, thus associating the message document to the device document;
m) procedure: this is the procedure model primary key for the procedure triggered with message delivery if applicable, thus associating the message document to the procedure document;
n) coverage: this is the coverage model primary key for the coverage triggered with message delivery if applicable, thus associating the message document to the coverage document;
o) fields: this is an array of message_field model primary key as the array key and the value of the field as provided by the sender as the array value (e.g., 'Urgent':'Yes'), thus associating the message document to one or more message field documents;
p) confirmed_by: this is a user model primary key for the individual who confirmed the message, thus associating the message document to the user document;
q) date_confirmed: this is a timestamp (e.g., UNIX timestamp) representing the time the message was confirmed;
r) canned_response: this is a canned_response model primary key for the canned response set by the message recipient; thus associating the message document to a canned response document containing a canned response message; and
s) bypass_coverage: this is used to indicate whether the message should bypass message routing.

An example of a filter model 410 as shown in FIG. 4B represents a user defined filter that can be used to, for example, trigger user defined message fields route a message based on a priority point system, or both. Properties (i.e., columns) within the message model are listed and described below:
a) _id: this is the filter model primary key and can be used to relate other documents to the filter model;
b) priority: this is an integer representing the priority points value of the filter.
c) user_id: this is user model primary key for the owner of the filter if the filter is an individual filter, thus associating the filter document to the user document;
d) group: this is a group model primary key for the owner of the filter if filter is a group filter, thus associating the filter document to the group document;
e) name: this is the textual representation of the filter name;
f) default_options: this is an array containing any default options (e.g., location, patient name, patient status, priority, calltype) as the array key, and the option value as the array value;
g) message_fields: this is an array containing message_field primary key as array key and field value as the array value, thus associating the filter document with one or more message field documents;
h) date_created: this is a timestamp (e.g., UNIX timestamp) representing the date the filter was created;
i) created_by: this is the user model primary key of the individual who created the filter, thus associating the filter document to the user document;
j) deleted: this indicates if the filter has been deleted;
k) date_deleted: this is a timestamp (e.g., UNIX timestamp) representing the date the filter was deleted if deleted;
l) deleted_by: this is the user model primary key of the individual who deleted the filter, thus associating the filter document to the user document;
m) last_edit_date: this is a timestamp (e.g., UNIX timestamp) representing the date the filter was last edited; and
n) last_edit_by: user model primary key of the individual who last edited the filter, thus associating the filter document to the user document.

Figure 4C:
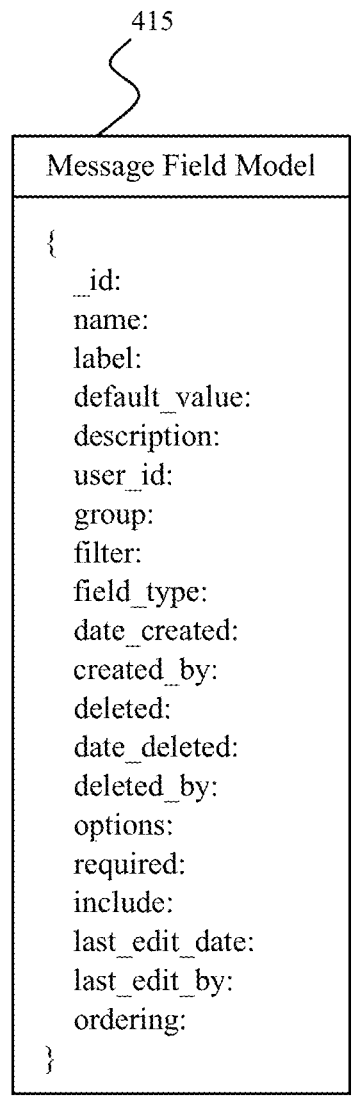

An example of a message field model 415 as shown in FIG. 4C represents user defined message fields which are added by default or conditionally to the message form. Properties (i.e., columns) within the message model are listed and described below:
a) _id: this is the mesage_field model primary key and can be used to relate other documents to the filter model;
b) name: this is the textual representation of the message_field name;
c) label: this is the textual representation of the message_field label;
d) default_value: this is the textual representation of the default value of the message_field if applicable;
e) description: this is textual representation of the description of the message_field if applicable;
f) user_id: this is user model primary key for the owner of the message_field if the message_field is an individual message_field, thus associating the message_field document to the user document;
g) group: this is a group model primary key for the owner of the message_field if the message field is an group message field, thus associating the message_field document to the group document;
h) filter: this is the filter model primary key of the filter used with the message field, this associating the message_field document with the filter document;
i) field_type: this is a textual representation of whether field is input or single select;
j) date_created: this is a timestamp (e.g., UNIX timestamp) representing the date the message field was created;
k) created_by: this is the user model primary key of the individual who created the message field, thus associating the message_field document to the user document;
l) deleted: this indicates if the message field has been deleted;
m) date_deleted: this is a timestamp (e.g., UNIX timestamp) representing the date the message field was deleted if deleted;
n) deleted_by: this is the user model primary key of the individual who deleted the message field, thus associating the message_field document to the user document;
o) options: this is an array containing select options if field_type is set to single select;
p) required: this indicates whether the field is required to be completed;

q) include: this indicates whether the field is to be displayed on the end user device receiving the message;
r) last_edit_date: this is a timestamp (e.g., UNIX timestamp) representing the date the message field was last edited.
s) last_edit_by: this is the user model primary key of the individual who last edited the message field, thus associating the message_field document to the user document; and
t) ordering: this indicates where field should be displayed on the message form.

Figure 4D:
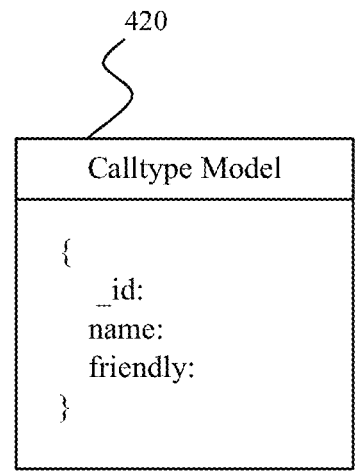

An example of a calltype model 420 as shown in FIG. 4D represents the individual initiating the message. Properties (i.e., columns) within the calltype model are listed and described below:
  a) _id: this is the calltype model primary key and can be used to relate other documents to the filter model; and
  b) name: this is the textual representation of the calltype name deliminated by underscore no capital letters.

Figure 4E:
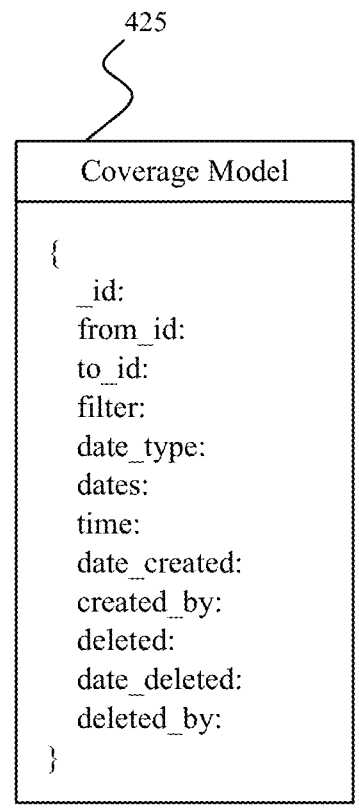

An example of a coverage model 425 as shown in FIG. 4E represents instances of provider/group coverage. Properties (i.e., columns) within the coverage are listed and described below:
  a) _id: this is the coverage model primary key and can be used to relate other documents to the coverage model;
  b) from_id: this is the user or group model primary key for the user/group being covered, thus associating the coverage document to a user document or a group document;
  c) to_id: this is a user model primary key of the individual providing coverage, thus associating the coverage document to a user document;
  d) filter: this is a filter model primary key of the filter being used with the coverage if applicable, thus associating the coverage document to a filter document;
  e) date_type: this indicates the date type of the coverage (e.g., persistent, single-instance, multiple-days, recurring specific days of month, recurring specific days of week);
  f) dates: this is an array of integers representing days of week/month;
  g) time: this is an array containing start and end times, "start/end" as array keys, timestamp (e.g., UNIX timestamp) representing times as values;
  h) date_created: this is a timestamp (e.g., UNIX timestamp) representing the date the coverage was created;
  i) created_by: this is the user model primary key of the individual who created the coverage, thus associating the coverage document to the user document;
  j) deleted: this indicates if the coverage has been deleted;
  k) date_deleted: this is a timestamp (e.g., UNIX timestamp) representing the date the coverage was deleted if deleted; and
  l) deleted_by: this is the user model primary key of the individual who deleted the coverage, thus associating the coverage document to the user document.

Figures 4F, 4G:
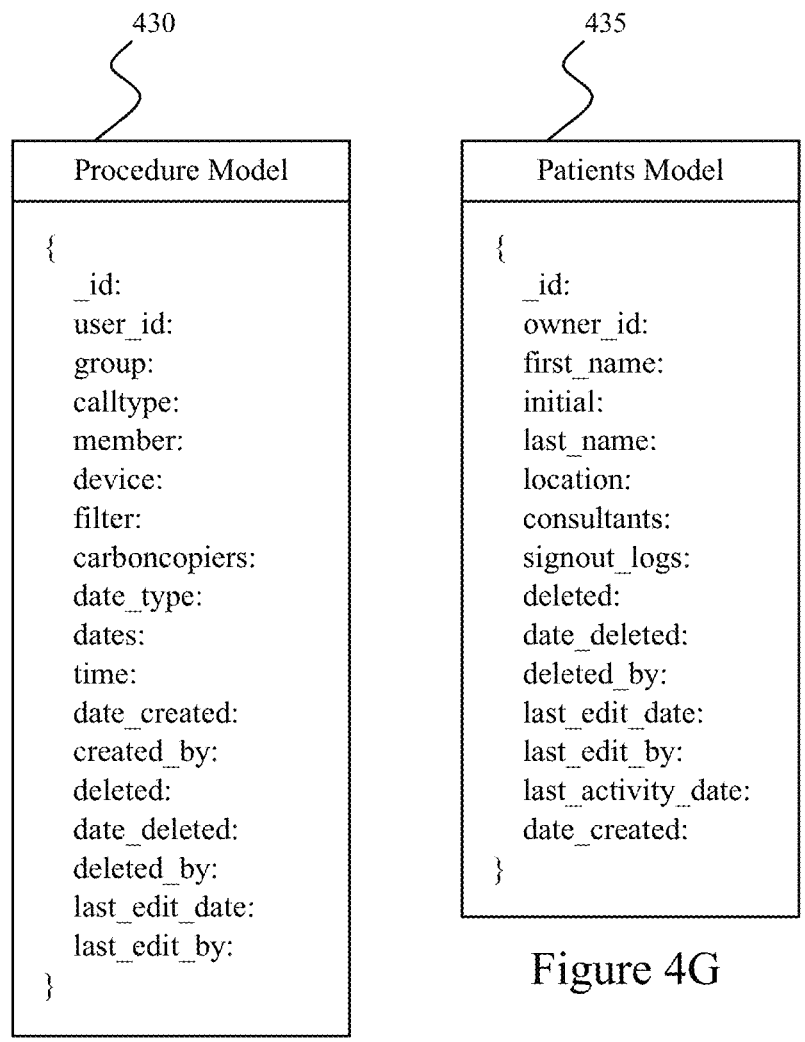

An example of a procedure model 430 as shown in FIG. 4F represents user defined device delivery instruction based on at least one of calltype, filter, or date(s). Properties (i.e., columns) within the procedure are listed and described below:
  a) _id: this is the procedure model primary key and can be used to relate other documents to the procedure model;
  b) user_id: this is the user model primary key of the owner of the procedure if the procedure is an individual procedure, thus associating the procedure document to a user document;
  c) group_id: this is a group model primary key of the owner of the procedure if the procedure is a group procedure, thus associating the procedure document to a group document;
  d) calltype: this is a calltype model primary key of the calltype used with the procedure; thus associating the procedure document to the calltype document;
  e) member: this is the user_member model primary key of the user_member to route the message to if applicable, thus associating the procedure document to the user member document;
  f) device: this is the device model primary key of the device to route the message to if applicable, thus associating the procedure document to the device document;
  g) filter: this is a filter model primary key of the filter being used with the procedure if applicable, thus associating the procedure document to a filter document;
  h) carboncopiers: this is an array of model user primary keys representing users which should receive a carbon copy of any message sent using the procedure, thus associating the procedure document with one or more user documents;
  i) date_type: this indicates the date type of the coverage (e.g., persistent, single-instance, multiple-days, recurring specific days of month, recurring specific days of week).;
  j) dates: this is an array of integers representing days of week/month;
  k) time: this is an array containing start and end times, "start/end" as array keys, timestamp (e.g. UNIX timestamp) representing times as values;
  l) date_created: this is a timestamp (e.g., UNIX timestamp) representing the date the procedure was created;
  m) created_by: this is the user model primary key of the individual who created the procedure, thus associating the procedure document to the user document;
  n) deleted: this indicates if the procedure has been deleted;
  o) date_deleted: this is a timestamp (e.g., UNIX timestamp) representing the date the procedure was deleted if deleted;
  p) deleted_by: this is the user model primary key of the individual who deleted the procedure, thus associating the procedure document to the user document;
  q) last_edit_date: this is a timestamp (e.g., UNIX timestamp) representing the date the procedure was last edited; and
  r) last_edit_by: this is the user model primary key of the individual who last edited the procedure, thus associating the procedure document to the user document;

An example of a patients model 435 as shown in FIG. 4G represents patients which have been created in the system. Patients can be created by sending a message or manually entering the information. Properties (i.e., columns) within the patients model are listed and described below:
  a) _id: this is the patient model primary key and can be used to relate other documents to the patient model;
  b) owner_id: this is the group model primary key for the group the patient belongs to, thus associating the patient document to the group document;
  c) first_name: this is the first name of the patient, which can be stored as an encrypted value;
  d) initial: this is the middle initial of the patient, which can be stored as an encrypted value;
  e) last_name: this is the last name of the patient, which can be stored as an encrypted value;

f) location: this is the facility model primary key for the facility where the patient is located, thus associating the location document to the facility document;
g) consultants: this is an array of user model primary keys representing the consultants assigned to the patient, thus associating the patient document to one or more user documents;
h) signout_logs: this is an array containing user model primary key as array key and user defined text as array value;
i) deleted: this indicates if the patient has been deleted;
j) date_deleted: this is a timestamp (e.g., UNIX timestamp) representing the date the patient was deleted if deleted;
k) deleted_by: this is the user model primary key of the individual who deleted the patient, thus associating the patient document to the user document;
l) last_edit_date: this is a timestamp (e.g., UNIX timestamp) representing the date the patient was last edited;
m) last_edit_by: this is the user model primary key of the individual who last edited the patient, thus associating the patient document to the user document;
n) last_activity_date: this is the timestamp (e.g., UNIX timestamp) representing the last time a message was sent concerning the patient; and
o) date_created: this is a timestamp (e.g., UNIX timestamp) representing the date the patient was created.

An example of a device model 440 as shown in FIG. 4H represents a user defined device used for message delivery, where users are also able to define method of delivery (e.g., secure SMS, conference, voice relay, etc.). Properties (i.e., columns) within the device model are listed and described below:
  a) _id: this is the patient model primary key and can be used to relate other documents to the device model;
  b) user_id: this is the user model primary key for the owner of the device, thus associating the device document to the user document;
  c) name: this is the textual representation of user defined device name; d) number: this is the 10 digit phone number if applicable;
  e) message: this is the textual user defined message shown to message sender if applicable;
  f) device_auth_type: this is the textual representation of how a message will be delivered (e.g., relay, conference, sms, etc.);
  g) device_type: this is the textual representation of the device type (e.g., sms, app, etc.);
  h) deleted: this indicates if the device has been deleted;
  i) date_deleted: this is a timestamp (e.g., UNIX timestamp) representing the date the device was deleted if deleted;
  j) deleted_by: this is the user model primary key of the individual who deleted the device, thus associating the device document to the user document;
  k) last_edit_date: this is a timestamp (e.g., UNIX timestamp) representing the date the device was last edited;
  l) last_edit_by: this is the user model primary key of the individual who last edited the device, thus associating the device document to the user document;
  m) resend_interval: this is the length of time the system waits before resending an unconfirmed message to this device;
  n) resend_count: this is the number of times the system resends a message to this device before calling to confirm receipt of message;
  o) missed_call: this is the instructions to perform in case of a missed call to this device;
  p) uuid: this is the unique identifier for the specific mobile device;
  q) pin: this is the pin number associated with the specific mobile device;
  r) push_token: this is the identifier for Apple to be able to send notifications to the device; and
  s) gcm_token: this is the identifier for Android to be able to send notifications to the device;
  t) An example of a user model as shown in FIG. 4I represents the base user within the system. Users can have a user_nurse, user provider, user_member, or user_agent associated with the user account. Properties (i.e., columns) within the device model are listed and described below:
  a) _id: this is the user model primary key and can be used to relate other documents to the user model;
  b) email: this is the user email address;
  c) lastlogin: this is the timestamp (e.g., UNIX timestamp) for the users last login;
  d) logins: this is the number of logind for the user;
  e) password: this is the user's password, that can be stored encrypted;
  f) username: this is the user's username;
  g) first_name: this is the users first name;
  h) middle initial: this is the users middle initial;
  i) last name: this is the users last name;
  j) group_id: this is the group model primary key for the group the user belongs to if applicable, thus associating the user document with the group document; and
  k) status: this is the user status within the system.

An example of a group model 450 as shown in FIG. 4J represents a group of providers which may have their own message fields and filters which are applied to all user accounts within the group. Properties (i.e., columns) within the group model are listed and described below:
  a) _id: this is the group model primary key and can be used to relate other documents to the group model;
  b) name: this is the name of the group;
  c) alt_name: this is the abbreviated group name;
  d) forwarding: this is an array with day of week as array key and another array as the array value containing a timestamp (e.g., UNIX timestamp) for a start and end date. This is used to route messages to a group forwarding center rather than an user's target device; and
  e) calltypes: this is an array containing a calltype model id as the array key and the corresponding friendly value of the calltype as the array key.

Figure 5:
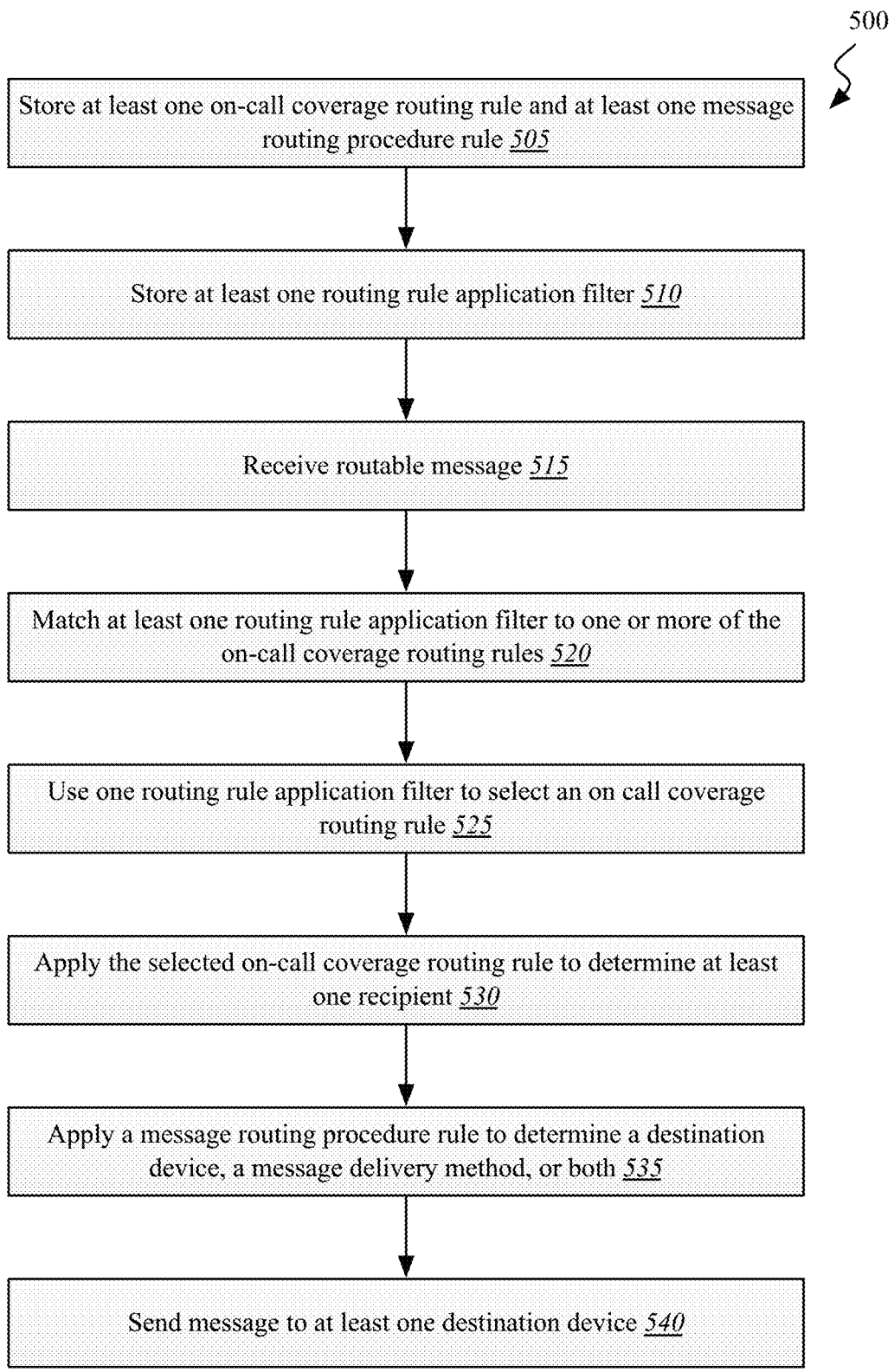
FIG. 5 is a flow diagram of an on-call coverage rule and application filter based method of routing messages to the mobile devices of FIG. 1.

Referring now to FIG. 5, method 500 may be carried out by a rule-based message routing and delivery system 100 according to various embodiments. The method 500 may, for example, be performed by a combination of one or more of the server computing devices of FIG. 1.

In certain embodiments, on-call coverage rules are stored and used to determine, at least in part, a message routing destination. Initially, at block 505, the coverage service, upon receiving a save coverage model request from client device 112 (see, e.g., FIG. 1) communicates with the persistence layer 306 (see, e.g., FIG. 3) via a database interface driver, passing a BSON object that constitutes, at least in part, an instance of a coverage model 425 (e.g., see FIG. 4). The persistence layer 306, in response to the request, saves the coverage model properties as a coverage document. In a manner similar to that described for the coverage model 425, a message routing procedure rule can also be saved as a procedure document in the persistence layer 306. At block

510, a routing application filter rule can also be stored as a filter document in the persistence layer 306.

At block 515 the messaging service 386 (see, e.g., FIG. 3) receives a routable message from a client device. The routable message can include, for example, a text message or a voice message. Upon receiving this message, at block 520, the coverage for the relevant message data for the associated group is retrieved. In certain implementation, this includes retrieving all group user_ids, determining the active coverages, and checking for time matches. The following is a portion of code that can perform the described functions in some embodiments:

```
public static function get_coverage_user ($to_user, $message_data, $first_run=TRUE, $timestamp=NULL)
{
   if( is_null($timestamp))
      $timestamp = time( );
   $filters = array( );
   $user_ids = array($to_user->pk( ));
   if($first_run === TRUE)
   {
      $user_ids[ ] = $to_user->group_id;
   }
   $CoverageCollection = Collection::instance('coverage');
   $CoverageWhere = array('to_id' => array('$in' => $user_ids), 'deleted' => 0);
   $CoverageResults = $CoverageCollection->get_all($CoverageWhere, array('_id'));
   $coverage_ids = array( );
   if($CoverageResults !== FALSE)
   {
      foreach($CoverageResults AS $CoverageResult)
         $coverage_ids[ ] = (string) $CoverageResult['_id'];
   }
   if(count($coverage_ids) <= 0)
      returnFALSE;
   $where = array(
      'coverage_id'    => array('$in' => $coverage_ids),
      'start_time'     => array(
          '$lte'       =>        $timestamp
      ),
      'end_time'                 => array(
          '$gte'       =>        $timestamp
      )
   );
   $CoverageCollection = Collection::instance('coverage_entry');
   $CoverageResults = $CoverageCollection->find_all($where);
   $message_filters = array( );
   $blind_coverage = array( );
   if($CoverageResults !== FALSE)
   {
      foreach($CoverageResults AS $coverage_entry)
      {
         $coverage = $coverage_entry->get_coverage( );
         /*if( ! $coverage->active_coverage(time( )))
             continue;*/
         if( ! empty($coverage->filter))
         {
            $Filter = Model::factory('filter', $coverage->filter);
            if($Filter->loaded( ))
            {
               if($Filter->matches($message_data))
               {
                  $priority =$Filter->priority_count( );
                  $message_filters[$priority] = $coverage;
               }
            }
         }
         else
         {
            if($coverage->to_id == $to_user->pk( ))
            {
               $blind_coverage['user'][ ] =$coverage;
            }
            elseif ($coverage->to_id == $to_user->group_id)
            {
               $blind_coverage['group'][ ] = $coverage;
            }
         }
      }
   }
```

At block 525, a routing rule application filter is used to select the coverage routing rule applicable to the message routing. The filter service 387 (see, e.g., FIG. 3) can determine a set of filters that match the retrieved coverage rules by assessing whether the filter message input conditions match the message content, such as the message fields. In some embodiments, filter conditions include logical operators that relate defined values to the values contained in the message. For example, operators can include equal to, not equal to, contains, and does not contain. Depending on the selected operator for a particular filter condition, the filter service 387 can determine if all the conditions are met for the application filter, and if so, include it in the pool of filters to be considered for selection by the coverage service 388. The following is a portion of code that can perform the described filter service 387 functions in some embodiments:

```
public function matches (Array $fields=array( ))
{
    if ( ! $this->loaded( ) ) return FALSE;
    //for direct admits
    if(array_key_exists('patient_direct_admit', $fields) AND $fields['patient_direct_admit'] == 1)
    {
        $fields['patient_status'] = 'established';
    }
    foreach ($this->default_options AS $field_name => $options)
    {
        $_weight_count = 1;
        if (array_key_exists($field_name, $fields))
        {
            $field_value = $fields[$field_name];
            switch ( $options['operator'] )
            {
                case '$eq':
                    $value = $options['value'];
                    if ($options['name'] = 'Patient')
                    {
                        if ($value[0] != $field_value) {
                            return FALSE;
                        }
                    }
                    elseif ($options['name'] == 'Calltype')
                    {
                        if ($value[0] != $field_value) {
                            return FALSE;
                        }
                    }
                    elseif ($options['name'] == 'Location')
                    {
                        $field_value = explode('|', $field_value);
                        if ( ! array_key_exists(1, $field_value))
                            $field_value[1] = '';
                        else
                            $_weight_count = 2;
                        $facility = array('facility' => $field_value[0], 'unit' => $field_value[1]);
                        $matches = FALSE;
                        //check to see if there's a facility with no unit
                        foreach($options['value'] AS $facility_data)
                        {
                            if (empty($facility_data['unit']) AND $facility_data['facility'] == $facility['facility'])
                                $matches = TRUE;
                        }
                        if ($matches === FALSE AND ! in_array($facility, $options['value']))
                            return FALSE;
                    }
                    elseif ($options['name'] == 'Priority')
                    {
                        if($options['value'] == 'yes')
                        {
                            $_weight_count = 50;
                        }
                    }
                    else
                    {
                        if ($value != $field_value) {
                            return FALSE;
                        }
                    }
                    break;
                case '$neq':
                    $value = $options['value'];
                    if ($options['name'] == 'Patient')
                    {
                        if ($value[0] == $field_value) {
                            return FALSE;
                        }
                    }
                    elseif ($options['name'] == 'Calltype')
                    {
                        if ($value[0] == $field_value) {
                            return FALSE;
                        }
                    }
                    elseif ($options['name'] == 'Location')
                    {
                        $field_value = explode('|', $field_value);
                        if ( ! array_key_exists(1, $field_value))
                            $field_value[1] = '';
                        else
                            $_weight_count = 2;
                        $facility = array('facility' => $field_value[0], 'unit' => $field_value[1]);
                        $matches = TRUE;
                        //check to see if there's a facility with no unit
                        foreach($options['value'] AS $facility_data)
                        {
                            if (empty($facility_data['unit']) AND $facility_data['facility'] == $facility['facility'])
                                $matches = FALSE;
                        }
                        if ($matches === FALSE OR in_array($facility, $options['value']))
                            return FALSE;
                    }
                    break;
                case '$in':
                    if ($options['name'] == 'Location')
                    {
                        $field_value = explode('|', $field_value);
                        if ( ! array_key_exists(1, $field_value))
                            $field_value[1] = '';
                        else
                            $_weight_count = 2;
                        $facility = array('facility' => $field_value[0], 'unit' => $field_value[1]);
                        $matches = FALSE;
                        //check to see if there's a facility with no unit
                        foreach($options['value'] AS $facility_data)
                        {
                            if (empty($facility_data['unit']) AND $facility_data['facility'] == $facility['facility'])
                                $matches = TRUE;
                        }
                        if ($matches === FALSE AND !
```

```
in_array($facility, $option['value']))
                        return FALSE;
                }
                else
                {
                    if ( ! in_array($field_value,
$options['value']) ) {
                        return FALSE;
                    }
                }
                break;
            case '$nin':
                if ($options['name'] == 'Location')
                {
                    if(empty($field_value))
                        return FALSE;
                    $field_value = explode('|',
$field_value);
                    if ( ! array_key_exists(1,
$field_value))
                        $field_value[1] = '';
                    else
                        $_weight_count = 2;
                    $facility = array('facility' =>
$field_value[0], 'unit' => $field_value[1]);
                    $matches = TRUE;
                    //check to see if there's a facility
with no unit
                    foreach($options['value'] AS
$facility_data)
                    {
                        if
(empty($facility_data['unit'] AND $facility_data['facility'] ==
$facility['facility'])
                            $matches =
FALSE;
                    }
                    if ($matches === FALSE OR
in_array($facility, $options['value']))
                        return FALSE;
                }
                else
                {
                    if ( in_array($field_value,
$options['value']) ) {
                        return FALSE;
                    }
                }
                break;
        }
    }
    else
    {
        if($field_name != 'priority' AND $field_name != 'calltype')
            return FALSE;
    }
    $this->_match_count += $_weight_count;
}
```

```
foreach ($this->message_fields AS $field_id => $options)
{
    if (array_key_exists($field_id, $fields))
    {
        switch ( $options['operator'] )
        {
            case '$eq':
                $value = $options['value'];
                if ($options['type'] == 'single-select') {
                    $value = $value[0];
                }
                if ($value != $fields[$field_id]) {
                    return FALSE;
                }
                break;
            case '$neq':
                $value = $options['value'];
                if ($options['type'] == 'single-select') {
                    $value = $value[0];
                }
                if ($options['value'] == $fields[$field_id]) {
                    return FALSE;
                }
                break;
            case '$nin':
                if ( ! in_array($fields[$field_id],
$options['value']) ) {
                    return FALSE;
                }
                break;
            case '$nin':
                if ( ! in_array($fields[$field_id],
$options['value']) ) {
                    return FALSE;
                }
                break;
        }
    }
    else
    {
        return FALSE;
    }
    $this->_match_count += 2;
}
return TRUE;
}
```

The selection of the routing rule application filter is based, in some instances, on assigning a priority value to the application filter, determining which of the application in the set of filters that match the retrieved coverage rules has the highest priority, then determining the final coverage rule and applicable coverage based, at least in part, on using the identified application filter. The following is a portion of code that can perform the described coverage service 387 (see, e.g., FIG. 3) function in some embodiments:

```
$FinalCoverage = FALSE;
$KeepChecking = FALSE;
if(count($message_filters) > 0)
{
    krsort($message_filters);
    foreach($message_filters AS $Coverage)
    {
        if($Coverage->loaded( ) AND $Coverage->deleted == 0)
        {
            $FinalCoverage = $Coverage;
            $KeepChecking = TRUE;
            break;
        }
    }
}
if ($FinalCoverage === FALSE)
{
    if (array_key_exists('user', $blind_coverage) AND
```

```
count($blind_coverage['user']) > 0)
    {
        ksort($blind_coverage['user']);
        $FinalCoverage = array_shift($blind_coverage['user']);
        $KeepChecking = TRUE;
    }
    else
    {
        if (array_key_exists('group', $blind_coverage) AND
count($blind_coverage['group']) > 0)
        {
            ksort($blind_coverage['group']);
            $FinalCoverage = array_shift($blind_coverage['group']);
            $KeepChecking = TRUE;
            //check if the coveree is a group
            /*$Coveree = $FinalCoverage->user('from');
            if($Coveree instanceof Model_Group)
                $KeepChecking = TRUE;
            unset($Coveree);*/
        }
    }
}
self::$user_check_count++;
if(self::$user_check_count > 10)
{
    mail('x@y.com','Infinite Recursion Schedule','There is a problem with infinite
schedule recursion for user ' . $to_user->pk( ) . ' ' . $to_user->first_name . ' ' . $to_user->
last_name);
    return FALSE;
}
if($KeepChecking === TRUE AND $FinalCoverage !== FALSE)
{
    $ChainUser = $FinalCoverage->user('from');
    if($ChainUser->loaded( ))
    {
        $Chained = self::get_coverage_user($ChainUser, $message_data,
FALSE, $timestamp);
        if($Chained !== FALSE)
        {
            return $Chained;
        }
    }
}
return $FinalCoverage;
}
```

Once the application filter is applied and the call coverage routing rule selected, a recipient can be determined 530 by the coverage service 388 (see, e.g., FIG. 3). At block 535, the delivery service 384 can select a message delivery procedure rule and determine at least one destination device associated with the recipient, a message delivery method, or both. Once these determinations are made, the messaging service 386 can prepare and transmit the message to the identified device in according to the selected delivery method 540. The sending of the message can, in some instances, involve a series of pre-send validation tasks prior to transmission. Tasks can include, for example, validation of the user originating the message request, validating the target recipient as a valid provider, validating the patient and create new patient if required, validating the location, facility, and unit, validating callback number, validating message contents, removing default options from _POST data, and checking if valid message fields remain in _POST data. Once validation is successful, the fields can be saved for the patient. Filters relating to location, patient, and patient status can be loaded, and the group forwarding enabled flag can be checked 708 (see, e.g., FIG. 7A). Where group forwarding is enabled, the message can be sent to a designated group staff member 710. If the message originated from a member of the same group as the targeted recipient 712, coverage can be bypassed and the message can be sent to the targeted recipient 714, 716. Carbon copies can be checked, and the message can be delivered to the appropriate devices associated with one or more recipients. In some instances, confirmation of a successful send event may be communicated to a device associated with the user sending the message.

Figure 6:
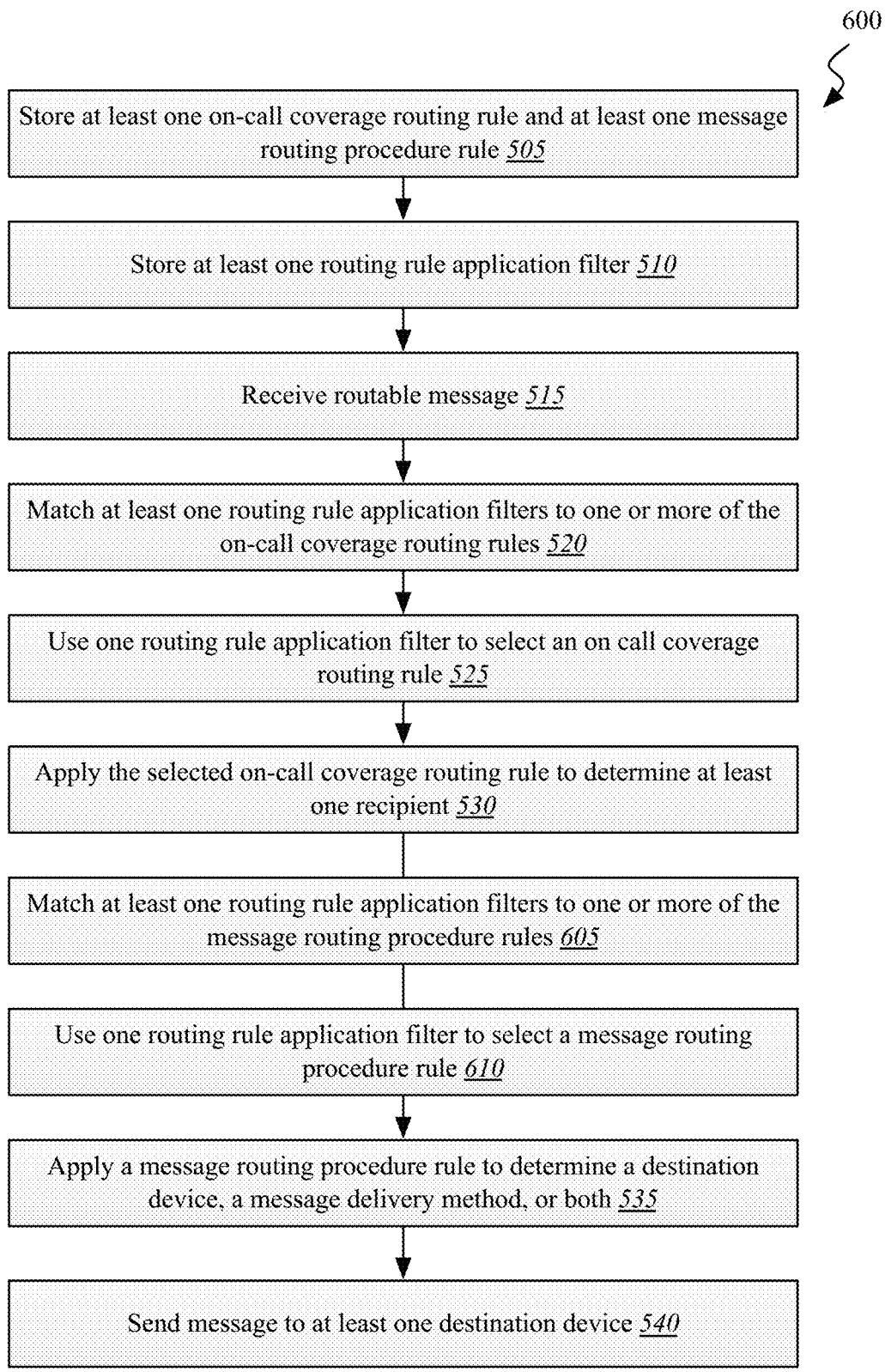
FIG. 6 is a flow diagram of an on-call coverage rule, delivery procedure rule, and application filter based method of routing messages to the mobile devices of FIG. 1.

Referring now to FIG. 6, much like the process for matching selecting and applying application filters to coverage rule determination, in some embodiments, delivery procedures are also determined, in part, through the user of rule application filters 605, 610. Where the message data involves filter application 605, 610 the process is the same as described for FIG. 5.

Delivery message procedures can include, but are not limited to:
  a) delivering to a designated device an SMS message that includes a secure link for viewing a message. This can involve sending a REST API call to a cloud communication service 371 such as Twilio, over HTTPS initiating the sending of the SMS message;
  b) notifying a call center agent to call a physician and verbally relay information provided in the message;
  c) notifying a call center agent to conference the message sender with the physician recipient; and
  d) sending a push notification via HTTPS to the appropriate notification server or service, such as the Apple Push Notification Service for pushing notification to iOS devices, or the Google Cloud Messaging service for pushing notification to Android devices.

Upon receiving this message, at block 605, the delivery procedure for the relevant message for the associated group is retrieved. In certain implementation, this includes retrieving all relevant group procedure ids and user procedure ids, determining the active procedures based on the procedure user and the call type. Call types can categorize the type of message originator, such as, for example:

a) Coroner's Office;
b) Nurse;
c) Physician;
d) Unit Coordinator;
e) Group Admin;
f) Group Operator;
g) Group Billing Admin;
h) Provider (Physician);
i) InPatient or Family Member;
j) OutPatient or Family Member;
k) InPatient Pharmacy;
l) Outpatient Pharmacy;
m) Quest Diagnostics & Other Labs;
n) OutPatient Radiology;
o) Home Health Agency;
p) Patient Scheduling;
q) Patient Cancellations;
r) Referrals;
s) Family Medical Leave ACT (FMLA);
t) Medical Records;
u) Medical Prior Authorizations;
v) Insurance Prior Authorizations;
w) Mortuary;
x) Personal Calls;
y) Chief of Medicine;
z) Prisoner; and
aa) Executive Health Resources.

The following is a portion of code that can perform the described delivery procedure service 389 (see, e.g., FIG. 3) functions in some embodiments:

```
/**
* Searches for $Users active procedure and returns it.
* @param Model_User $User
* @param string $calltype
* @param string $filter
* @return Model_Procedure
*/
public static function get_active_procedure (Model_User $User,
$calltype,
$message_data)
{
    //grab a list of all this users procedure ids also the group
    $ProcedureCollection = Collection::instance('procedure');
    $where = array(
        '$or' => array(
            array('user_id' => $User->pk()),
            array('user_id' => $User->group_id)
        ),
        'calltype'=>   $calltype,
        'deleted' => 0
    );
    $Results = $ProcedureCollection->get_all($where, array('_id'));
    if ($Results !== FALSE)
    {
        $procedure_ids = array( );
        foreach ($Results AS $Result)
            $procedure_ids[ ] = (string) $Result['_id'];
    }
    else
    {
        return FALSE;
```

-continued

```
    }
    $current_time = time( );
    $EntryCollection = Collection::instance('procedure_entry');
    $where = array(
        'procedure_id'   => array('$in' => $procedure_ids),
        'start time'     => array('$lte' => $current_time),
        'end_time'                 => array('$gte' => $current_time)
    );
    $Entries = $EntryCollection->find_all($where);
    if($Entries !== FALSE)
    {
        $message_filters = $GroupProcedures =
$UserProcedures = array( );
        foreach ($Entries AS $Entry)
        {
            if ( ! empty($Entry->filter))
            {
                $Filter = Model::factory('filter', $Entry->filter);
                if ($Filter->loaded( ))
                {
                    if ($Filter->matches($message_data))
                    {
                        $message_filters[$Filter->priority] =
$Entry->get_procedure( )->get_final_procedure($calltype,
$message_data);
                    }
                }
            }
            else
            {
                $EntryProcedure = $Entry->get_procedure( );
                if ($EntryProcedure->group == TRUE)
                {
                    $GroupProcedures[$EntryProcedure-
>date_created] = $EntryProcedure->get_final_procedure($calltype,
$message_data);
                }
                else
                {
                    $UserProcedures[$EntryProcedure-
>date_created] = $EntryProcedure->get_final_procedure($calltype,
$message_data);
                }
            }
        }
        //krsort
        if(count($GroupProcedures) > 0)
        {
            ksort($GroupProcedures);
            $GroupProcedure = array_pop($GroupProcedures);
        }
        if(count($UserProcedures) > 0)
        {
            ksort($UserProcedures);
            $UserProcedure = array_pop($UserProcedures);
        }
        if (count($message_filters) > 0)
        {
            krsort($message_filters);
            return array_shift($message_filters);
        }
        elseif ( isset($GroupProcedure) AND !
is_null($GroupProcedure) AND
( ! isset($UserProcedure) OR is_null($UserProcedure)))
            return $GroupProcedure;
        elseif ( isset($UserProcedure) AND ! is_null($UserProcedure))
            return $UserProcedure;
        else
        {
            return FALSE;
        }
    }
    else
    {
        return FALSE;
    }
}
/**
* Iterates through member forward procedures
```

-continued

```
* @param type $calltype
* @param type $message_data
* @return type
*/
public function get_final_procedure($calltype, $message_data)
{
    if ( ! empty($this->member))
    {
        $ProcedureUser = Model::factory('user', $this->member);
        $Procedure = self::get_active_procedure($ProcedureUser,
            $calltype,
$message_data);
        if($Procedure !== FALSE AND $Procedure->loaded( ))
            return $Procedure->get_final_procedure($calltype,
$message_data);
        else
        {
            return $this;
        }
    }
    else
    {
        return $this;
    }
}
```

Figure 7A:
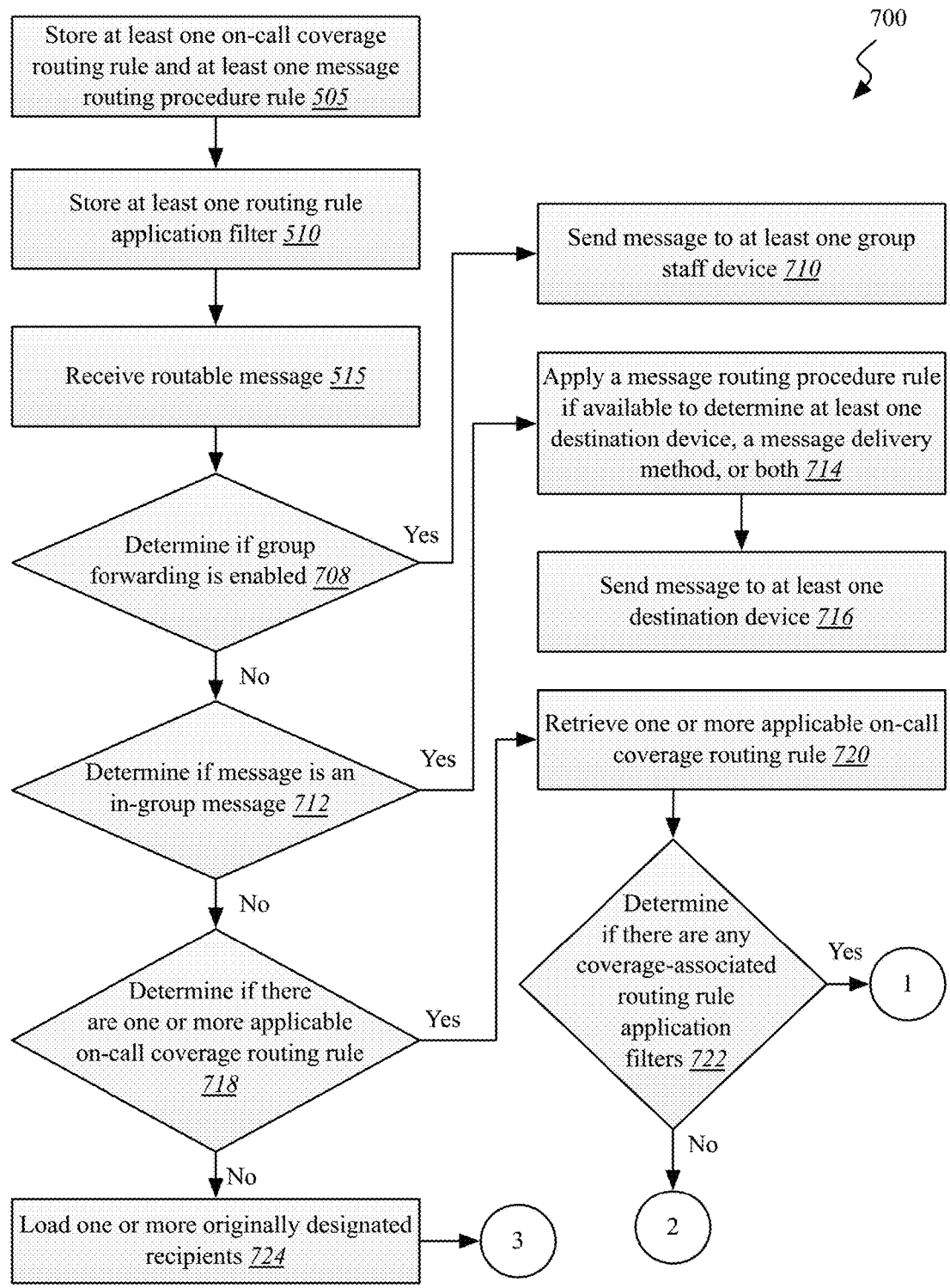
FIG. 7A through FIG. 7C is a detailed flow diagram of an on-call coverage rule, delivery procedure rule, and application filter based method of routing messages to the mobile devices of FIG. 1.
Figure 7B:
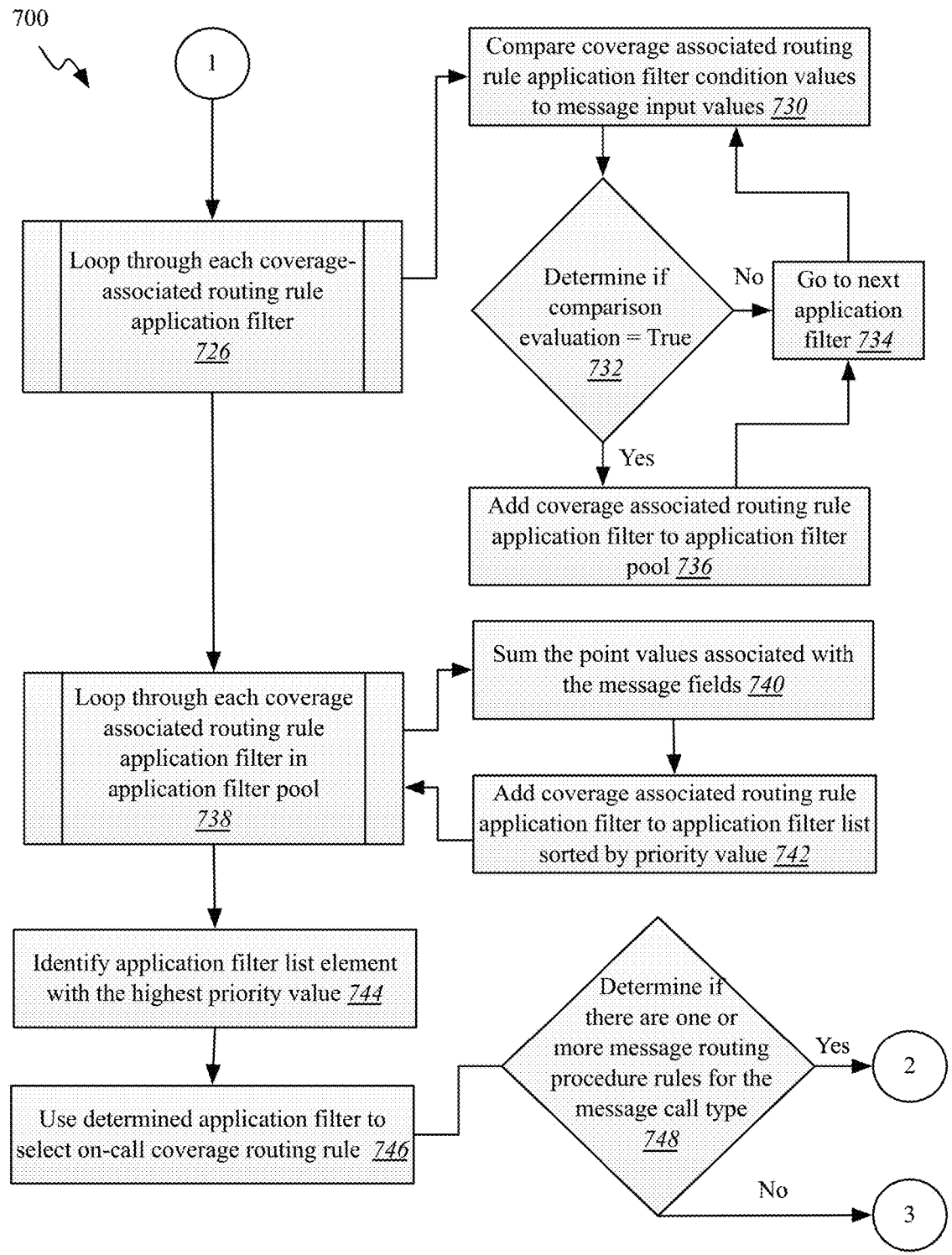
Figure 7C:
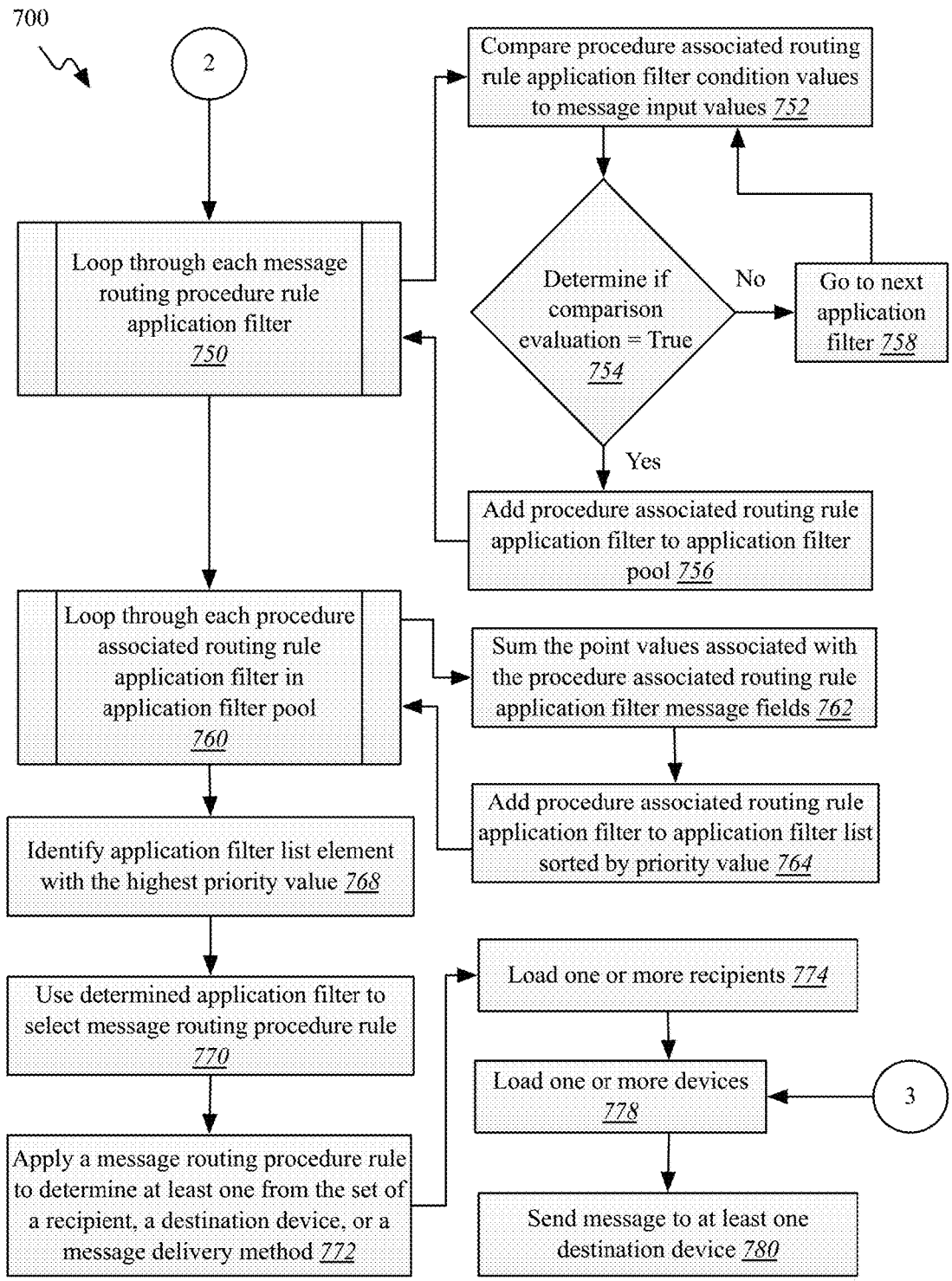

Referring now to FIG. 7A through FIG. 7C, a detailed exemplary embodiment of the method described in FIG. 6 is disclosed. The initial steps 505, 510, including receiving a routable message 515, are the same as described for FIG. 5 and FIG. 6. Once the message is received, a variety of preliminary checks are conducted in advance of progressing to coverage analysis and routing determination. At block 708, the group forwarding enabled parameter is checked, and if set to enable, coverage is bypassed and the message is sent directly to at least one group staff member 710. If, on the other hand, the group forwarding enabled parameter is not set to enabled, the message is checked to determine if the group is an in-group message 712. If so, a message routing procedure rule is applied if available to determine at least one destination device, a message delivery method, or both 714. Once this determination is made, the message is sent to the device indicated by the applied procedure, or alternatively, to the default device where there is no available procedure 716.

If both of the previous checks return false, then the coverage service 388 (see, e.g., FIG. 3) can determine if there are any applicable on-call coverage routing rules 718. If there are applicable on-call coverage routing rules, the coverage service 388 can retrieve the coverage documents from the coverage database 397 and access the properties to obtain the relevant on-call coverage routing rules 720.

Before applying any of the on-call coverage routing rules, the filter service 387 (see, e.g., FIG. 3) determines if there are any coverage-associated routing rule application filters that need to be evaluated 722. If any application filters require evaluation, the filter service 387 can loop through each coverage-associated routing rule application filter 726 to determine if the application rules conditions are met. First, the filter service 387 compares the coverage associated routing rule application filter condition values to input values contained in the message 730. If the evaluation is true 732, the coverage-associated routing rule application filter is added to the application filter pool 736 for priority analysis, and the next coverage-associated routing rule application filter is evaluated 734.

Once all coverage-associated routing rule application filters have been evaluated, the filter service 387 (see, e.g., FIG. 3) loops through each coverage associated routing rule application filter in application filter pool 738 and determines a priority value based on summing the point values associated with the message fields 740. The filter service 387 then sorts the application filters by priority 742 and identifies the one with the highest priority 744. This identified coverage-associated routing rule application filter is then used to select an on-call coverage routing rule 746.

After coverage application is accomplished, the delivery service 384 (see, e.g., FIG. 3) determines if there are any message routing procedure rules for the message call type for the user 748. If there are any message routing procedure rules, an analysis and prioritization of any routing procedure rule application filters 750, 752, 754, 756, 758, 760, 762, 764, 768 is performed in a manner similar to that just described for the coverage-associated routing rule application filters 726, 730, 732, 734, 736, 738, 740, 742, 744. The determined rule is used to select a message routing procedure rule 770, which when applied, determines a recipient, a destination device, or a message delivery method 772. At this point, one or more recipients are loaded 774, associated devices are loaded 778, and the message is send to the destination devices 780 in accordance with the appropriate delivery method.

By default, an account will not have any filters. A filter is used to define a logical operation that compares a defined message attribute or value to the corresponding message attribute or value according to logical operator. If the operation returns true, the rule associated with the filter is available for application if selected by the controlling service. Filters may have associated or calculated priorities. In some instances, message fields are assigned a point value, the sum of the point values being the filter priority. Filters can be created per provider, or for the entire group, such as at the group level and provider level.

Figure 8:
FIG. 8 is a screen capture of a portion of new message field creation page for interfacing with the messaging service of FIG. 3.

Referring now to FIG. 8, a new message field page displays editable controls for creating a message field. Message fields are fields included in messages that can be used to receive input values for filter condition evaluation. In some instances, message fields can include text input fields or single select list value fields. In other instances, additional types of message fields can be made available, including toggle selections, multi-select list value fields, and the like. Message fields can apply to either a group or an individual. In the case of the individual, the message fields will appear in a send message page after the physician's name is selected in the physician name selection control.

Figure 9:
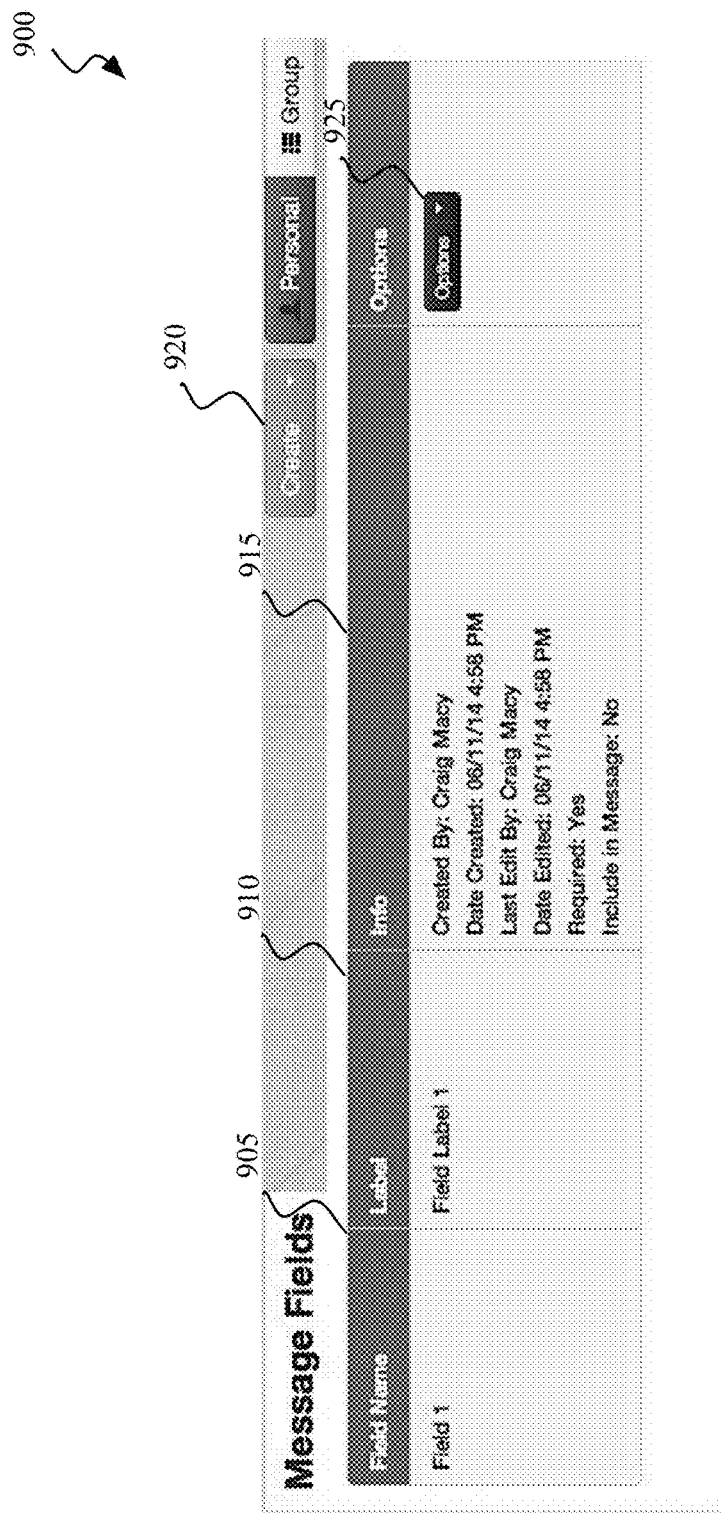
FIG. 9 is a portion of summary page displaying a list of the message fields created through the message field creation page of FIG. 8.

Referring now to FIG. 9, in some implementations, a portion of a summary page 900 displays a list of the message fields created through the new message field page 800 (see, e.g., FIG. 8) just discussed, including both personal message fields and group message fields. The display can include, the message field name 905, the message field label 910, and metadata information associated with the message field 915. Detection of the selection event associated with the create button 920 displays the new message field page 800. Detection of the selection event associated with the options button 925 displays a pop menu (not shown) that includes an edit message field selection and a delete message field selection.

Figure 10:
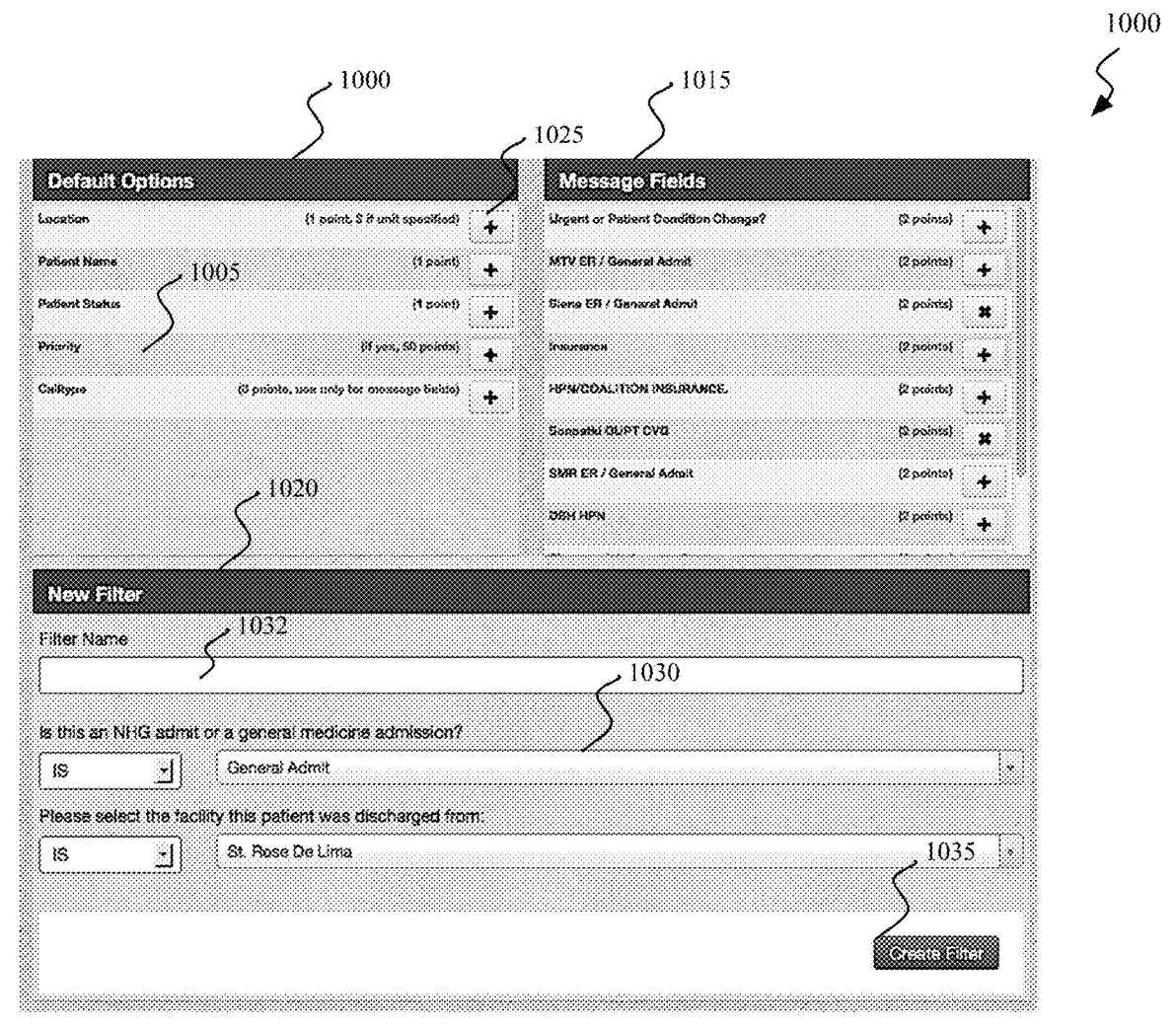

Referring now to FIG. 10, in some embodiments, a new filter creation page displays default filter options and custom message fields for use in constructing filter statements. Default options 1000 can include, for example, location, patient name, patient status, and call type. In addition, in some instances, a priority option 1005 can be assigned a large point value such that a user can effectively designate the filter as having the highest priority. In addition to the default options 1005, in certain implementations, custom message fields 1015 can be included in the filter statements. Some examples of custom fields include Urgent or Patient Condition Change and Insured. Message routing can be conditioned upon the message values set for these message fields.

Upon detection of the click even associated with the plus button, 1025, an appropriate statement 1030 relating to the attribute or field is added to the New Filter section of the page 1020. Multiple statements can be added to the filter. In some embodiments, the statements are connected by an 'AND' connector. In other embodiments, other connectors can be defined, parentheticals can be added, or both. In some implementations, selectable logical operators determine the logical test for each statement, such as IS (i.e. equal to), IS NOT (i.e. not equal to), IN (i.e. contains), and NOT IN (i.e. does not contain). A filter name edit control 1032 can receive a text string identifying the filter, and upon detection of the selection event associated with the create filter button 1035, BSON object is sent to the filter service 386 (see, e.g., FIG. 3) over HTTPS directing the filter service 386 to store the filter document in the filter database 395.

Figure 11:
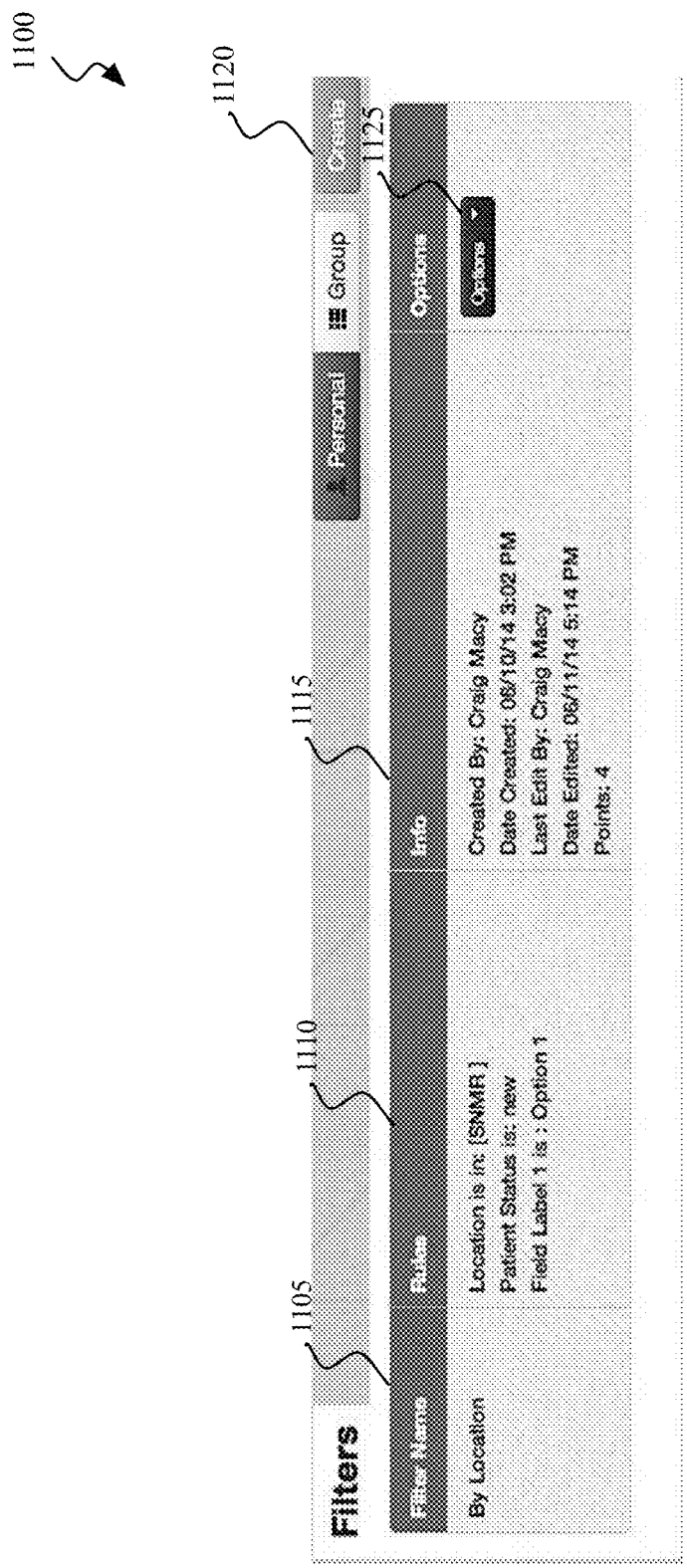
FIG. 11 is a portion of summary page displaying a list of the filters created through the new filter creation page of FIG. 10.

Referring now to FIG. 11, in some implementations, a portion of a summary page 1100 displays a list of the filters created through the new filter creation page just discussed, including both personal filters and group filters. The display can include, the filter name 1105, the filter statements 1110, and metadata information associated with the filter 1115. In addition, the summed points can be displayed indicating the priority of the filter. Detection of the selection event associated with the create button 1120 displays the new filter creation page 1000 (see, e.g., FIG. 10). Detection of the selection event associated with the options button 1125 displays a pop menu (not shown) that includes an edit filter selection and a delete filter selection.

Figure 12:
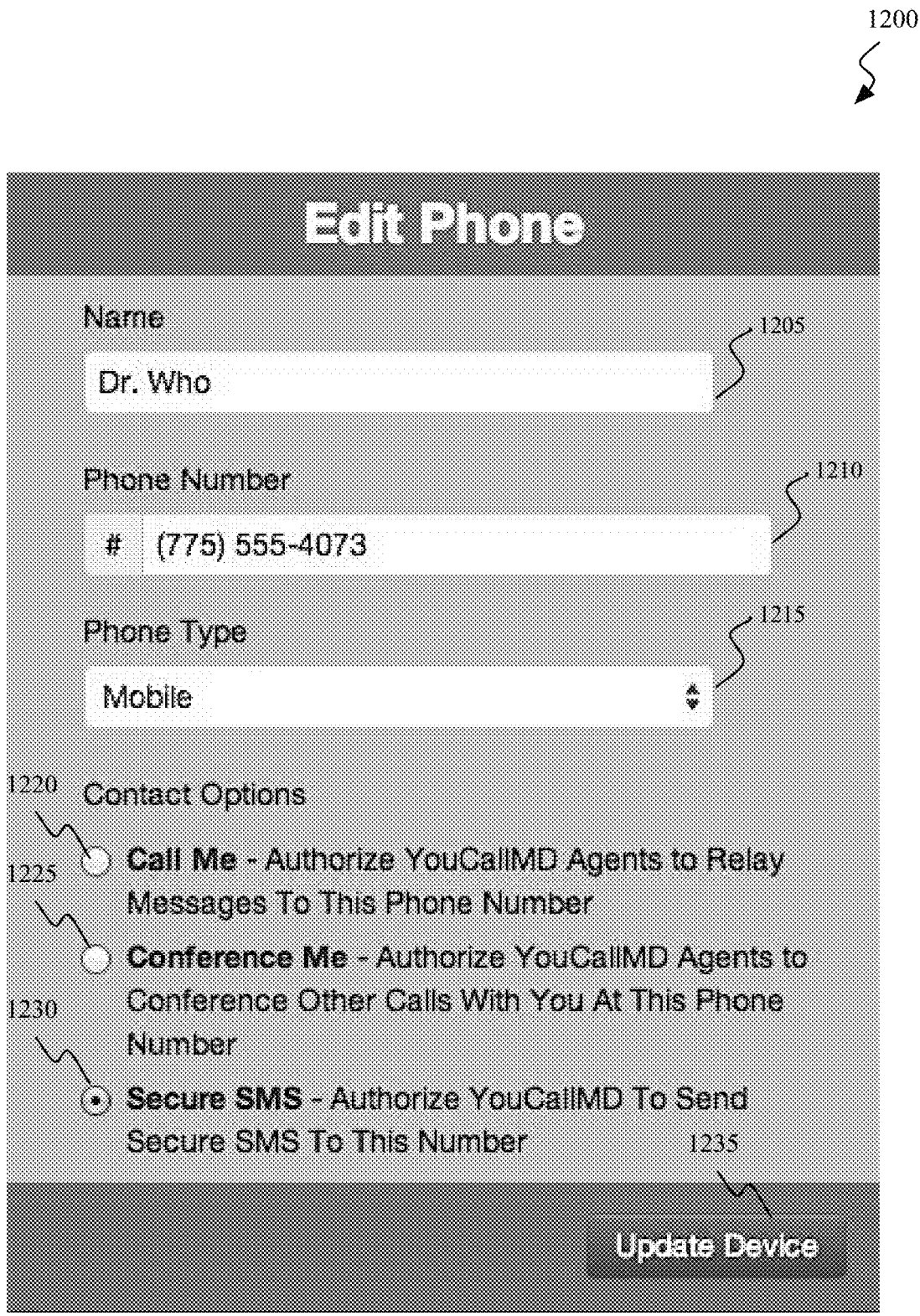
FIG. 12 is a screen capture of an edit device view for interfacing with the delivery service of FIG. 3 on the mobile device of FIG. 1.

Referring now to FIG. 12, an edit device view 1200 displays controls for configuring the default delivery method for the device. The default delivery method will control the delivery method to the device absent the application of a message delivery procedure rule dictating an alternative delivery method. The edit device view can include edit controls for receiving a device name 1205, a device phone number 1210, a phone type 1215, and contact options (i.e. delivery method). Three of the four delivery methods previously discussed are displayed in this example 1220, 1225, 1230. In some embodiments, an additional option is displayed for selecting app messaging where the device is capable of running the system app and receiving push notifications.

Figure 13:
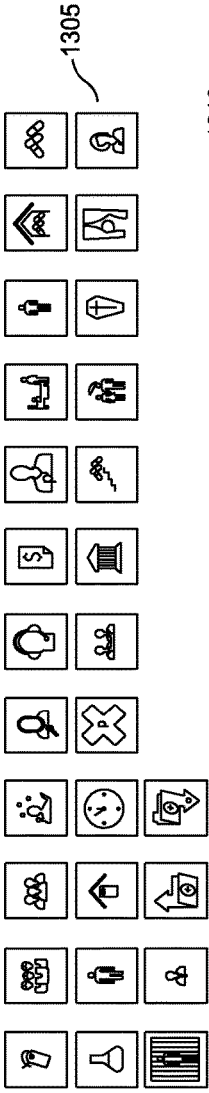
FIG. 13 is a screen capture of an edit procedure page for interfacing with the delivery procedure service of FIG. 3.

Referring now to FIG. 13, an edit procedure page 1300 displays various edit controls for creating message delivery procedure rules. In some cases, a series of icons 1305 or other selection controls, such as a selection list 1400 (e.g. see FIG. 14) are provided that allow for the selection of a call type. In certain instance, the call type is an indication of the origin of a message, although it will be readily understood that call type need not be restricted to only message origin. A filter selection control 1310 can allow for the selection of one or more rule application filters to be used in determining whether a message delivery procedure rule will be applied. Various date option selections 1315 can be displayed to control the time periods when the procedure will be active and available for selection. In addition, selectable target devices can be displayed for the procedure to control where messages are delivered when the procedure is applied.

Figure 15:
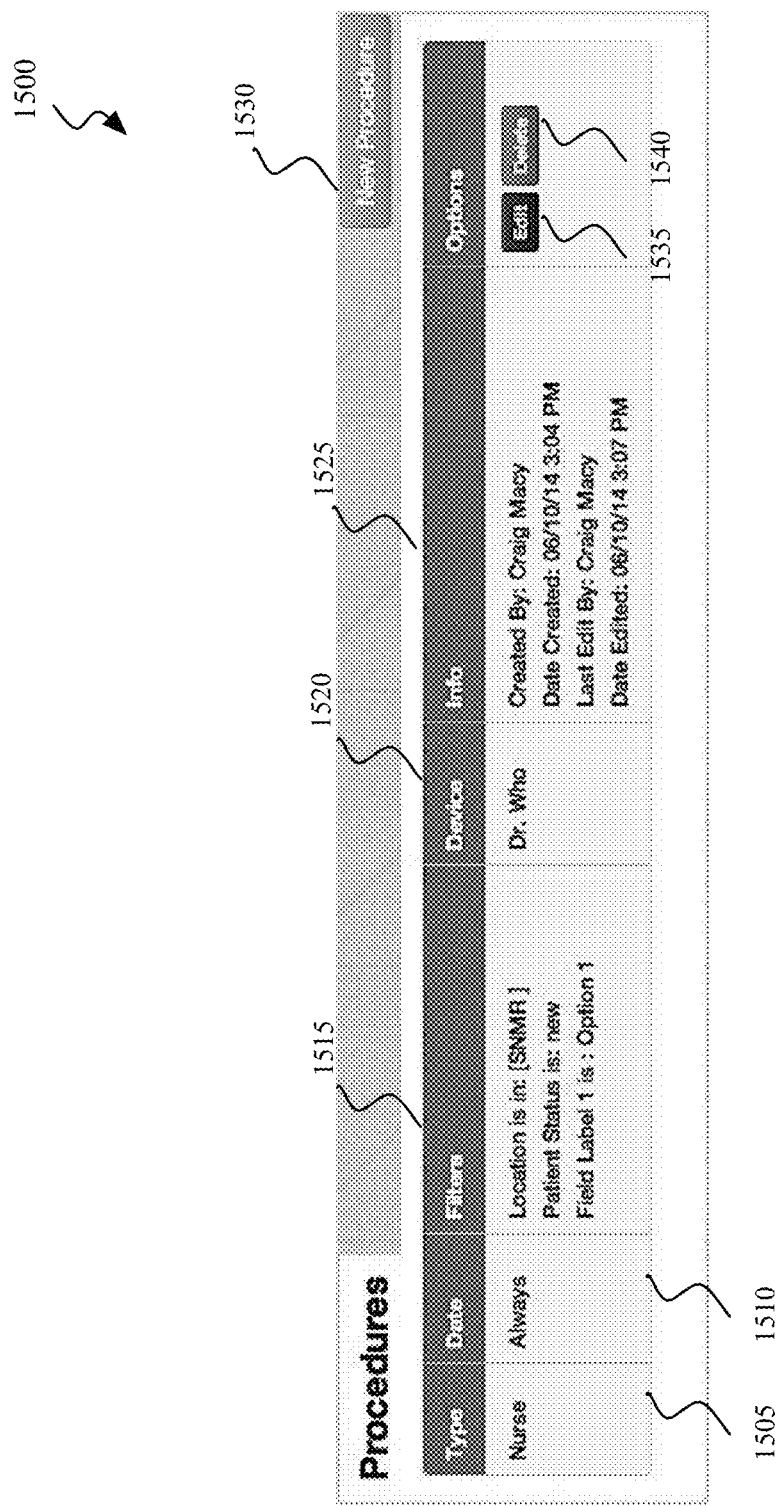
FIG. 15 is a portion of summary page displaying a list of the procedures created through the edit procedure page of FIG. 13.

Referring now to FIG. 15, in some implementations, a portion of a summary page 1500 displays a list of the procedures created through the new procedure page just discussed. The display can include, the call type 1505, the date or time period when the procedure is active and available for selection by a controlling system service 1510, any selected filter statements 1515, the target device 1520 and metadata information associated with the filter 1525. Detection of the selection event associated with the new procedure button 1530 displays the edit procedure page 1300. Detection of the selection event associated with the edit procedure button 1530 displays the edit procedure page 1300 populated with the saved values of the procedure. Detection of the selection event associated with the delete button 1540 displays deletes the procedure.

Figure 16:
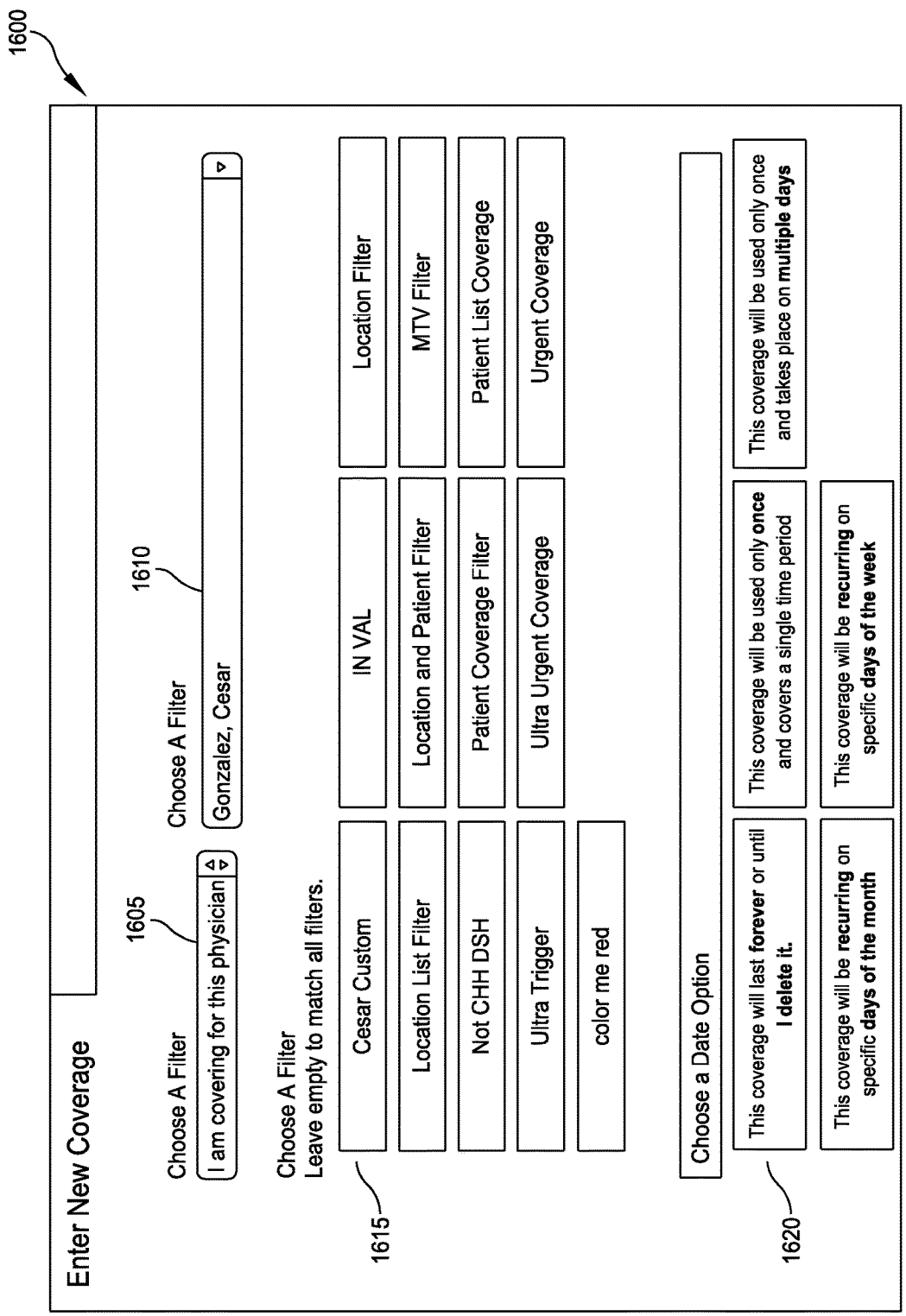
FIG. 16 is a screen capture of an enter new coverage page for interfacing with the coverage service of FIG. 3.

Referring now to FIG. 16, the enter new coverage page 1600 displays various controls for configuring coverage. The coverage type control 1605 receives the selection value indicating whether the coverage type will be a physician covering for the user or the user covering for another physician. The physician selection control 1610 receives the name of the physician covering for the user, or being covered by the user, depending on the coverage type selection. Selectable application filters 1615 can be displayed that can determine, in part, whether the coverage rule will be applied to message routing. Like the edit procedure page 1300, various date option selections 1620 can be displayed to control the time periods when the coverage rule will be active and available for application to message routing.

Figure 17:
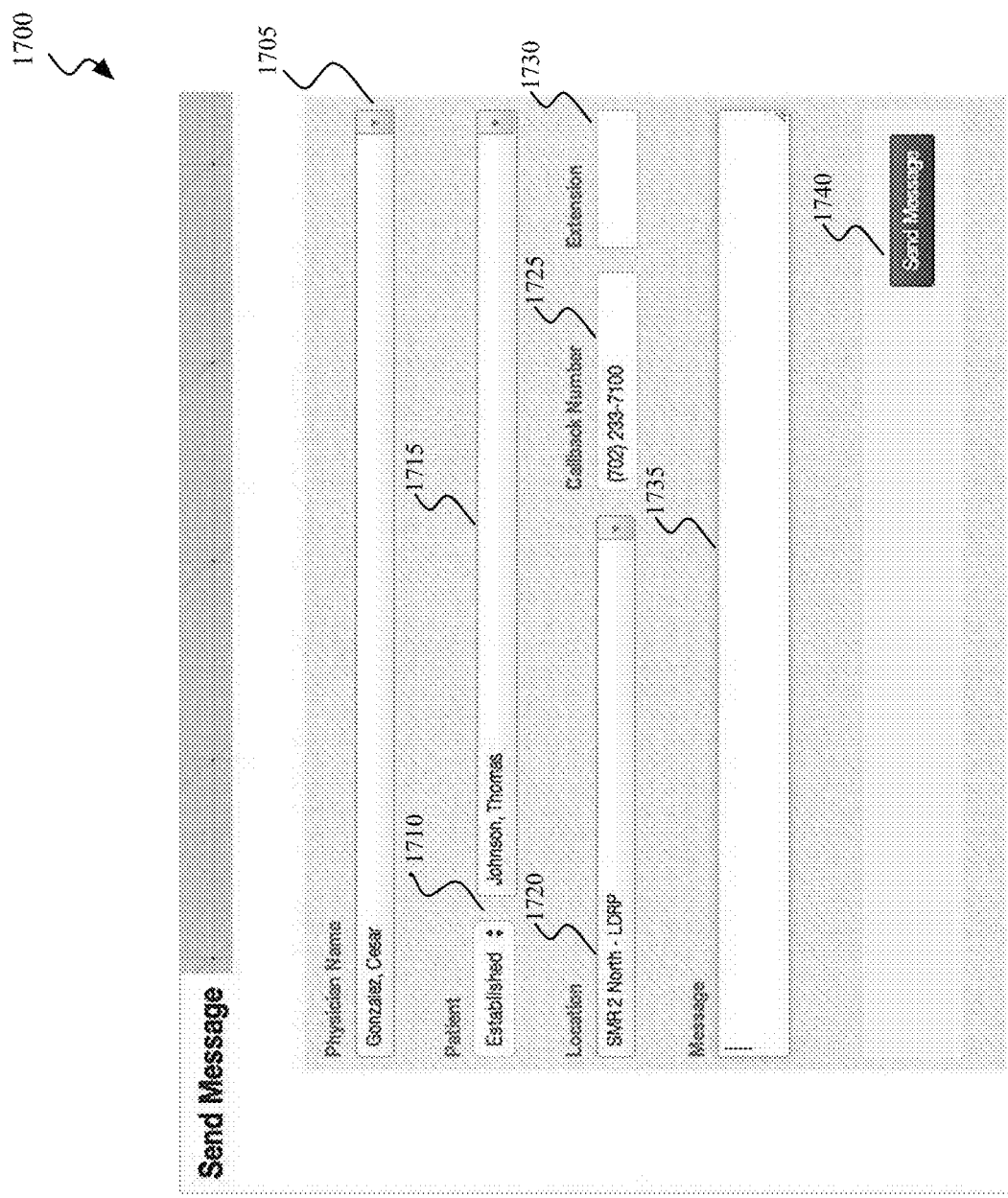
FIG. 17 is a screen capture of a physician send message page for interfacing with the message service of FIG. 3.

Referring now to FIG. 17 the process for message routing begins with the submission of message to the system for delivery to a recipient. Send message interfaces can be tailored to specific users and computing devices. For example, in some implementations, a physician send message interface 1700 can be tailored to messaging likely performed by physicians, such as sending in-group messages to other physicians. In this example, the interface includes a physician name selection field for the selection of a physician recipient 1705. If this is an in-group message, the in-group check previously discussed can bypass coverage routing, instead sending the message directly to the selected physician. Other fields to be completed and validated by the messaging service (see, e.g., FIG. 3) 386 can include a patient status field 1710 (e.g. new|established-|none), the patient name 1715, the location 1720, a callback number and extension 1725, 1730, and the message content 1735. Detection of the selection event associated with the Send Message button 1740 sends BSON object to the messaging service 386 over HTTPS initiating the message routing and delivery processes discussed previously 500, 600 (see, e.g., FIG. 5 and FIG. 6).

Figure 18:
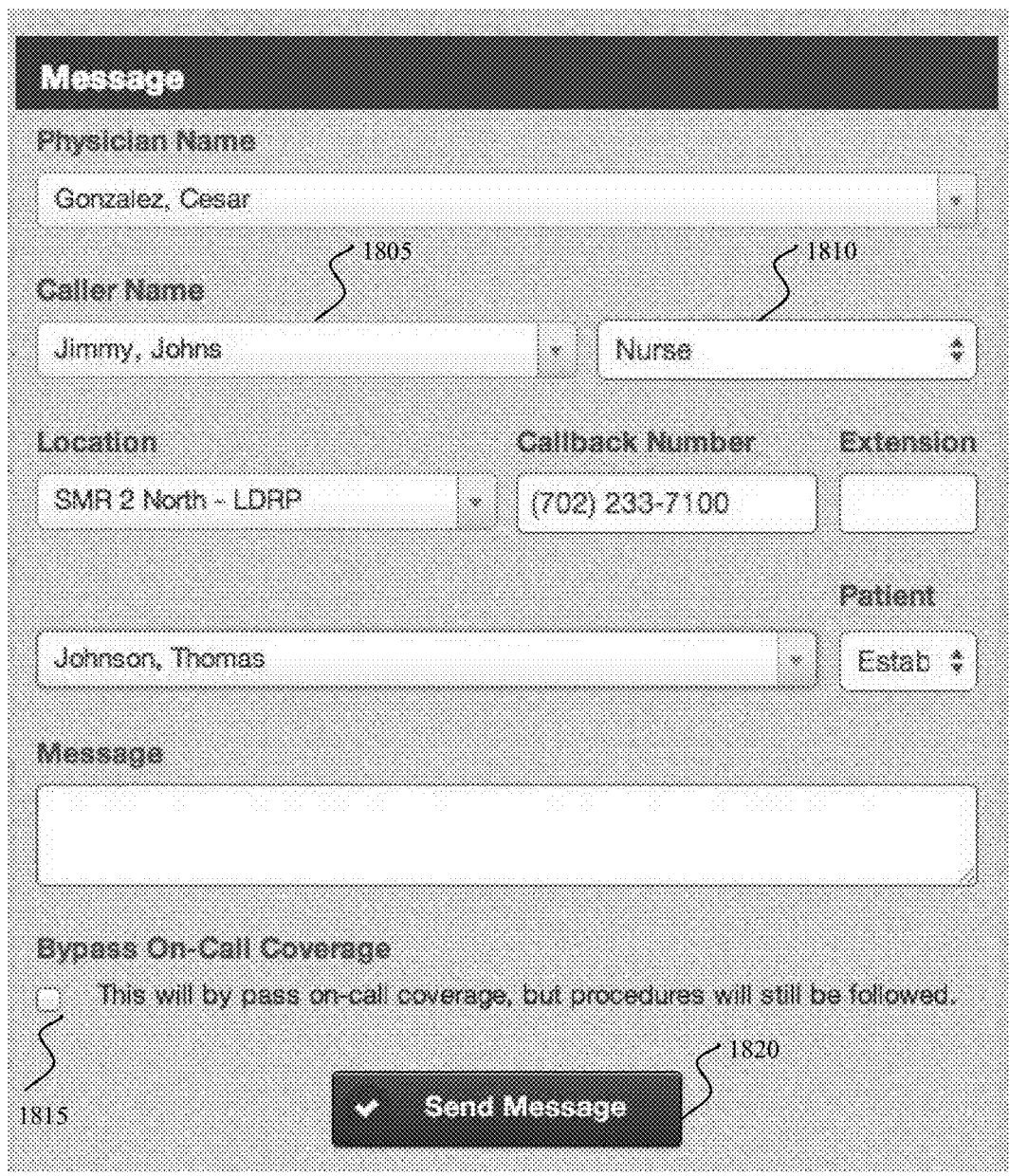
FIG. 18 is a screen capture of a call center agent send message page for interfacing with the message service of FIG. 3.

Other message submitting interfaces can be made available that are tailored to non-physicians, such as nurses and call center agents. For example, referring now to FIG. 18, a call center agent message submission interface 1800 may include many of the same message fields, but may also include additional fields, such as the name of the caller originating the message 1805, the call type (e.g. Nurse) 1810, and a bypass coverage option 1815. Detection of the selection event associated with the send message button 1820 sends BSON object to the messaging service 386 over HTTPS initiating the message routing and delivery processes discussed previously 500, 600 (see, e.g., FIG. 5 and FIG. 6).

User authentication can be enforced by the user service 385 (see, e.g., FIG. 3), thus helping to protect patient privacy and conform to regulatory requirements, such as those mandated by HIPAA. Some fields, such as name fields 1705, 1715, 1805 can implement embedded field search capabilities, helping to reduce data entry errors and improve performance. Once physician is selected, patient selections can be made available, and appropriate custom message fields can be displayed and completed. As an example of the process for sending messages, a nurse can:
 a) enter log on credentials;
 b) search for and select physician's name;
 c) select a patient's name from established the patient list or add a new patient;
 d) complete custom message fields (e.g. room number);
 e) complete message content;
 f) update contact number if needed;
 g) send message; and
 h) receive confirmation of send success.

In some instances, the message sender will receive direct confirmation that the message was sent from the messaging service 386 (see, e.g., FIG. 3). In addition, or alternatively, the message sender can check for message confirmation via the system inbox or, referring now to FIG. 19, in the message listing on the message log page 1900. In some instances confirmation occurs once the physician has confirmed that he has viewed the message. A date and time will be shown if confirmed, otherwise the message will state 'Unconfirmed' 1905.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures may be implemented to achieve the same functionality.

On reading this disclosure, those of skill in the art will recognize that many of the components discussed as separate units may be combined into one unit and an individual unit may be split into several different units. Further, the various functions could be contained in one computer or spread over several networked computers and/or devices. The identified components may be upgraded and replaced as associated technology improves, advances are made in computing technology, or based on a developers skills or preferences.

The process parameters, functions, system features, and sequence of steps described and/or illustrated herein are given by way of example only and may be varied and mixed and matched as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, the functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems, their components, and methods and various embodiments with various modifications as may be suited to the particular use contemplated.

The systems disclosed herein provide a novel and highly useful user interface and methods of use of the interface. See the Provisional Patent Application incorporated by reference in the "Cross-Reference to Related Application" section above.

In addition, the systems disclosed (including if desired those incorporated by reference as stated above) can be used to provide a business model (and method) in which a system provider provides the automated messaging and information delivery system to customers or licensees such as healthcare operations or providers. The system provider can charge the healthcare operations or providers, including, if desired, at much lower cost per message or information delivery event or period of use than has been the case with conventional physical answering and message delivery services. Because of the significantly increased efficiency of the system in delivering messages, such system can be provided at lower cost (if desired) to those utilizing the system while still being profitable for the system provider.

The model (and method) can include, if desired, a physical answering and messaging service in the event the automated system indicates to such service that a message recipient has not received a message intended for the recipient. Such a system can thus be much more efficient, developing revenues from licensing or other provisioning or providing of the automated system component and, if implemented, the physical answering and messaging service as well. If desired, the total cost of providing the automated system and/or physical service to third party healthcare operations and providers also can be lower while remaining profitable for the provider the system and/or service.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. An automated method of selecting a medical professional and routing and delivering a message to the selected medical professional, the method comprising:

receiving coverage routing rules and delivery procedure rules from a device operated by a recipient or an administrator,
  wherein the coverage routing rules and delivery procedure rules are received in real-time via a mobile device interface, workstation interface, or browser-based interface,
  wherein the recipient is an on-call healthcare professional,
  wherein the coverage routing rules are received pursuant to a save coverage model request from the device and specify a message routing destination comprising a message recipient or group of message recipients,
    wherein the coverage routing rules that are received pursuant to a save coverage model request specify active coverages,
    wherein the active coverages include the type or types of coverages, the timeframe or timeframes associated with the coverages, the recipient or group of recipients associated with coverages, and a patient or patients associated with coverages,
  wherein the delivery procedure rules specify how a message is to be delivered to an end user and include one or more of
    delivery of SMS messages to one or more mobile devices;
    delivery of secure SMS messages via secure links to the one or more mobile devices;
    delivery of transcribed voice message as a secure SMS message to the one or more mobile devices;
    delivery of application messages to the one or more mobile devices;
    delivery of messages to one or more system message inboxes; and
    initiation of a conference call with a message originator;
storing the coverage routing rules and delivery procedure rules in a persistence layer of one or more database servers,
  wherein the coverage routing rules are saved as a coverage document,
  wherein the delivery procedure rules are saved as a procedure document;
receiving configurable rule application filters which control the application of the coverage routing rules and/or delivery procedure rules;
  wherein the rule application filters include filter conditions,
  wherein the filter conditions each include logical operators that relate defined values in the particular filter to values contained in a message;
  wherein the filter conditions are constructed using default message fields and/or custom message fields;
storing the rule application filters in the one or more database servers;
  wherein the rule application filters are saved as a filter document;
receiving a message to be routed in accord with the coverage routing rules and delivery procedure rules as determined by the rule application filters;
  wherein the received message includes message fields and each field is assigned a received message input value,
  wherein the message is received from a device associated with a sender;
determining a plurality of rule application filters to apply to the received message, the determination comprising defining a logical operator that compares a defined message attribute or value to a corresponding message attribute or value, wherein the logical operators comprising equal to, not equal to, contains, and does not contain;
pursuant to the comparison returning true, adding the plurality of filters to a pool of rule application filters;
prioritizing the pooled rule application filters,
  wherein prioritizing comprises assigning a priority value to each of the pooled rule application filters and determining which of the pooled rule application filters has the highest priority;
  wherein each priority value is determined by summing the received message input value associated with the message fields;
  wherein the prioritized rule application filter having the highest priority is then implemented to select the coverage routing rule and the message routing procedure rule associated with the filter;
determining, by the rule application filters, coverage routing rules and delivery procedure rules to apply to a received message;
retrieving the determined coverage routing rules and delivery procedure rules from the one or more database servers;
applying the coverage routing rules and delivery procedure rules to the received message,
  wherein the coverage routing rules specify the recipient or group of recipients,
  wherein the delivery procedure rules specify the destination device and delivery method;
determining whether a recipient is on-call and to whom the message should be delivered using the applied coverage routing rules;
determining, based on the determined recipient, one or more devices and/or delivery methods to send the message based on the delivery procedure rules;
validating the sender of the message as a valid sender, the determined recipient as a valid provider, the patient as an existing or new patient, a callback number, and message content,
  wherein if the validation fails, the message is not sent;
determining whether group forwarding is enabled, the group forwarding specifying whether the message can be sent to a designated group of recipients,
  wherein if the message originated from a member of the group as the target recipient, coverage can be bypassed and the message sent to the target recipient,
pursuant to the validation and group forwarding determination, transmitting the message to the determined recipient or group of recipients using the determined one or more devices and/or delivery methods,
  wherein a send event is transmitted to the device associated with the sending entity indicating that the message has been sent;
receiving acknowledgement that the end user received the message,
  wherein the message receipt, delivery, and acknowledgement are performed in compliance with HIPAA requirements.

2. The method of claim 1 further comprising:
matching at least one rule application filter to one or more of the message routing procedure rules; and
using one of the matched rule application filters to select one of the message routing procedure rules.

3. The method of claim 1 further comprising, if group forwarding is enabled, sending the message to at least one of a practice group staff computing device.

4. The method of claim 1 further comprising determining if the message is an in-group message.

5. The method of claim 2 further comprising adding the matched message routing procedure rules and rule application filters to a matched rule application filter pool.

6. The method of claim 1 further comprising adding matched rule application filters to a matched rule application filter pool.

7. The method of claim 1 wherein the secure SMS message includes a secure link to a transcribed voice message.

8. The method of claim 1, further comprising transmitting at least one thousand routable messages received from a plurality of originating client computing devices to a plurality of destination computing devices associated with a plurality of recipients, wherein:

the at least one thousand routable messages received from a plurality of originating client computing devices are received within a five consecutive minute period of time; and the at least one thousand routable messages are transmitted within the five consecutive minute period of time.

\* \* \* \* \*

UNITED STATES PATENT AND TRADEMARK OFFICE
CERTIFICATE OF CORRECTION

PATENT NO.        : 10,521,559 B1
APPLICATION NO.   : 14/304675
DATED             : December 31, 2019
INVENTOR(S)       : E. Ed Soumi, Matthew Pham and Cesar Omar Gonzalez Page 1 of 1

It is certified that error appears in the above-identified patent and that said Letters Patent is hereby corrected as shown below:

In the Specification

Column 28, 2 lines above Line 45, delete "S" and insert --$-- between "(" and the word "UserProcedures"

Column 28, 1 line below Line 45, delete "S" and insert --$-- between "(" and the word "UserProcedures"

Column 28, Line 55, delete "S" and insert --$-- between the first instance of "(" and the word "UserProcedure"

Column 28, Line 55, delete "S" and insert --$-- between the second instance of "(" and the word "UserProcedure"

Signed and Sealed this
Seventeenth Day of March, 2020

Andrei Iancu
*Director of the United States Patent and Trademark Office*